(12) United States Patent
Phaneuf et al.

(10) Patent No.: US 10,406,528 B1
(45) Date of Patent: Sep. 10, 2019

(54) NON-CONTACT TEMPERATURE CONTROL SYSTEM FOR MICROFLUIDIC DEVICES

(71) Applicant: National Technology & Engineering Solutions of Sandia, LLC, Albuquerque, NM (US)

(72) Inventors: Christopher Phaneuf, Livermore, CA (US); Chung-Yan Koh, Dublin, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 187 days.

(21) Appl. No.: 15/669,426

(22) Filed: Aug. 4, 2017

Related U.S. Application Data

(60) Provisional application No. 62/370,843, filed on Aug. 4, 2016.

(51) Int. Cl.
*G01N 21/35* (2014.01)
*G01N 21/64* (2006.01)
(Continued)

(52) U.S. Cl.
CPC ............. *B01L 7/52* (2013.01); *B01L 3/50273* (2013.01); *C12Q 1/6846* (2013.01); *G01N 21/35* (2013.01); *G01N 21/64* (2013.01); *B01J 2219/0097* (2013.01); *B01L 2300/0627* (2013.01); *B01L 2300/0803* (2013.01); *B01L 2300/168* (2013.01); *B01L 2300/1861* (2013.01); *B01L 2300/1872* (2013.01); *B01L 2400/0409* (2013.01); *C12Q 1/6848* (2013.01); *G01N 15/1484* (2013.01); *G01N 21/359* (2013.01); *G01N 21/6428* (2013.01); *G01N 27/44791* (2013.01); *G01N 27/44795* (2013.01); *G01N 2015/045* (2013.01)

(58) Field of Classification Search
CPC ............. G01N 21/64; G01N 2015/045; G01N 21/6428; G01N 15/1484; G01N 21/35; G01N 21/359; G01N 27/44791; G01N 27/44795; B01L 2300/1861; B01L 3/50273; B01J 2219/0097; C12Q 1/6848
See application file for complete search history.

(56) References Cited

U.S. PATENT DOCUMENTS 3,555,284 A 1/1971 Anderson
3,744,974 A 7/1973 Maddox
(Continued)

FOREIGN PATENT DOCUMENTS

WO WO-2008/143578 11/2008
WO WO-2009/098237 8/2009

OTHER PUBLICATIONS

U.S. Appl. No. 13/423,008, filed Mar. 16, 2012, Koh et al.
(Continued)

*Primary Examiner* — Jennifer Wecker
(74) *Attorney, Agent, or Firm* — Helen S. Baca

(57) ABSTRACT

The present invention relates to a temperature control system for a microfluidic device. The system allows for non-contact heating by employing an infrared emitter. In some instances, the system can be used in conjunction with a centrifugal microfluidic device. Optionally, a mask can be implemented to provide selective heating of desired assay areas of the device.

20 Claims, 15 Drawing Sheets

(51) Int. Cl.
    *B01J 19/00*     (2006.01)
    *B01L 3/00*      (2006.01)
    *B01L 7/00*      (2006.01)
    *C12Q 1/6844*    (2018.01)
    *C12Q 1/68*          (2018.01)
    *G01N 15/04*         (2006.01)
    *C12Q 1/6848*        (2018.01)
    *G01N 27/447*        (2006.01)
    *G01N 15/14*         (2006.01)
    *G01N 21/359*        (2014.01)

(56) References Cited

U.S. PATENT DOCUMENTS

| | | | |
|---|---|---|---|
| 4,125,375 | A | 11/1978 | Hunter |
| 4,156,570 | A | 5/1979 | Wardlaw |
| 4,554,071 | A | 11/1985 | Ruijten et al. |
| 4,656,143 | A | 4/1987 | Baker et al. |
| 4,683,579 | A | 7/1987 | Wardlaw |
| 4,844,818 | A | 7/1989 | Smith |
| 5,279,936 | A | 1/1994 | Vorpahl |
| 5,635,362 | A | 6/1997 | Levine et al. |
| 5,705,628 | A | 1/1998 | Hawkins |
| 5,882,903 | A | 3/1999 | Andrevski et al. |
| 5,892,577 | A | 4/1999 | Gordon |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 6,960,449 | B2 | 11/2005 | Wang et al. |
| 7,033,747 | B2 | 4/2006 | Gordon et al. |
| 7,157,049 | B2 | 1/2007 | Valencia et al. |
| 7,312,085 | B2 | 12/2007 | Chou et al. |
| 7,332,326 | B1 | 2/2008 | Kellogg et al. |
| 7,758,810 | B2 | 7/2010 | Lee et al. |
| 8,337,775 | B2 | 12/2012 | Pugia et al. |
| 8,945,914 | B1 | 2/2015 | Schaff et al. |
| 8,962,346 | B2 | 2/2015 | Schaff et al. |
| 9,186,668 | B1 | 11/2015 | Schaff et al. |
| 9,244,065 | B1 | 1/2016 | Schaff et al. |
| 9,304,128 | B1 | 4/2016 | Koh et al. |
| 9,304,129 | B2 | 4/2016 | Schaff et al. |
| 9,500,579 | B1 | 11/2016 | Coza |
| 9,702,871 | B1 | 7/2017 | Koh et al. |
| 2001/0055812 | A1 | 12/2001 | Mian et al. |
| 2002/0098535 | A1 | 7/2002 | Wang et al. |
| 2002/0106786 | A1 | 8/2002 | Carvalho et al. |
| 2002/0137068 | A1 | 9/2002 | Haugland et al. |
| 2002/0151043 | A1 | 10/2002 | Gordon |
| 2002/0153251 | A1 | 10/2002 | Sassi et al. |
| 2002/0164659 | A1 | 11/2002 | Rao et al. |
| 2002/0170825 | A1 | 11/2002 | Lee et al. |
| 2003/0013203 | A1 | 1/2003 | Jedrzejewski et al. |
| 2003/0078499 | A1* | 4/2003 | Eppstein .......... A61B 1/313 600/439 |
| 2003/0124719 | A1 | 7/2003 | Woodside |
| 2003/0203504 | A1 | 10/2003 | Hefti |
| 2004/0072278 | A1 | 4/2004 | Chou et al. |
| 2005/0186685 | A1 | 8/2005 | Kange et al. |
| 2005/0215410 | A1 | 9/2005 | Merino et al. |
| 2005/0282220 | A1 | 12/2005 | Prober et al. |
| 2006/0171654 | A1 | 8/2006 | Hawkins et al. |
| 2008/0108047 | A1 | 5/2008 | Woodside |
| 2008/0149484 | A1 | 6/2008 | Tolley et al. |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1 | 12/2009 | Hinnah et al. |
| 2010/0068754 | A1 | 3/2010 | Kirakossian |
| 2010/0120596 | A1 | 5/2010 | Froman et al. |
| 2010/0151560 | A1 | 6/2010 | Wo et al. |
| 2010/0302539 | A1* | 12/2010 | Myrick .......... G01J 3/02 356/326 |
| 2011/0045958 | A1 | 2/2011 | Pedrazzini |
| 2014/0273241 | A1 | 9/2014 | Ochranek et al. |
| 2015/0360225 | A1 | 12/2015 | Schaff et al. |
| 2016/0061829 | A1 | 3/2016 | Schaff et al. |
| 2016/0178619 | A1 | 6/2016 | Koh et al. |

OTHER PUBLICATIONS

U.S. Appl. No. 13/941,186, filed Jul. 12, 2013, Koh et al.
U.S. Appl. No. 14/090,040, filed Nov. 26, 2013, Koh et al.
U.S. Appl. No. 14/957,405, filed Dec. 2, 2015, Koh.
Abi-Samra et al., "Infrared controlled waxes for liquid handling and storage on a CD-microfluidic platform", Lab on a Chip, 2011, vol. 11, pp. 723-726.
Abi-Samra et al., "Electrochemical velocimetry on centrifugal microfluidic platforms", Lab on a Chip, 2013, vol. 13, pp. 3253-3260.
Ahanotu et al., "Staphylococcal enterotoxin B as a biological weapon: recognition, management, and surveillance of *Staphylococcal enterotoxin*", Applied Biosafety, 2006, vol. 11 (3), pp. 120-126.
Albrecht et al., "Micro free-flow IEF enhanced active cooling and functionalized gels", Electrophoresis, 2006, vol. 27, pp. 4960-4969.
Amasia et al., "Centrifugal microfluidic platform for rapid PCR amplification using integrated thermoelectric heating and ice-valving", Sensors and Actuators B, 2012, vol. 161, pp. 1191-1197.
Amersham Biosciences AB, "Percoll: Methodology and Applications", Handbook No. 18-1115-69 (Ed. AC), 2001, Uppsala, Sweden, pp. 1-84.
Amukele et al., "Ricin A-chain activity on stem-loop and unstructured DNA substrates", Biochemistry, 2005, vol. 44(11), pp. 4416-4425.
Andersson et al., "Parallel nanoliter microfluidic analysis system", Analytica; Chemistry, 2007, vol. 79(11), pp. 4022-4030.
Baldwin, "How Hofmeister ion interactions affect protein stability", Biophysical Journal, 1996, vol. 71, pp. 2056-2063.
Ball et al., "Quenching of unincorporated amplification signal reporters in reverse-transcription loop-mediated isothermal amplification enabling bright, single-step, closed-tube, and multiplexed detection of RNA viruses".
Analytical Chemistry, 2016, vol. 88, pp. 3562-3568.
Berlier et al., "Quantitative comparison of long-wavelength Alexa Fluor dyes to Cy dyes: fluorescence of the dyes and their bioconjugates", Journal of Histochemistry and Cytochemistry, 2003, vol. 51(12), pp. 1699-1712.
Berry et al., "One-step purification of nucleic acid for gene expression analysis via immiscible filtration assisted by surface tension", Lab on a Chip, 2011, vol. 11(10), pp. 1747-1753.
Boyko et al., "Cell-free DNA—a marker to predict ischemic brain damage in a rat stroke experimental model", Journal of Neurosurgery and Anesthesiology, 2011, vol. 23(3), pp. 222-228.
Brigotti et al., "Shiga toxin 1 acting on DNA in vitro is a heat-stable enzyme not requiring proteolytic activation", Biochimie Journal, 2004, vol. 86(45), pp. 305-309.
Buck et al., "Design strategies and performance of custom DNA sequencing primers", Biotechniques, 1999, vol. 27(3), pp. 528-536.
Cabrera et al., "Formation of natural pH gradients in a microfluidic device under flow conditions: model and experimental validation", Analytical Chemistry, 2001, vol. 73(3), pp. 658-666.
Carney, "Rapid diagnostic tests employing latex particles", Analytical Proceedings, 1990, vol. 27, pp. 99-100.
Chen et al., "Wirelessly adaptable heater array for centrifugal microfluidics and *Escherichia coli* sterilization", 35th Annual International Conference of the IEEE EMBS, held Jul. 3-7, 2013 in Osaka, Japan, pp. 5505-5508.
Churchill et al., "Detection of Listeria monocytogenes and the toxin listeriolysin O in food", Journal of Microbiological Methods, 2006, vol. 64(2), pp. 141-170.
Cui et al., "Multistage isoelectric focusing in a polymeric microfluidic chip", Analytical Chemistry, 2005, vol. 77(24), pp. 7878-7886.
Curtis et al., "A molecular approach to bioseparations: protein-protein and protein-salt interactions", Chemical Engineering Science, 2006, vol. 61, pp. 907-923.

(56) References Cited

OTHER PUBLICATIONS

Czeiger et al., "Measurement of circulating cell-free DNA levels by a new simple fluorescent test in patients with primary colorectal cancer", American Journal of Clinical Pathology, 2011, vol. 135(2), pp. 264-270.
Das et al., "Effects of separation length and voltage on isoelectric focusing in a plastic microfluidic device", Electrophoresis, 2006, vol. 27(18), pp. 3619-3626.
Endo et al., "RNA N-glycosidase activity of ricin A-chain. Mechanism of action of the toxic lectin ricin on eukaryotic ribosomes", The Journal of Biological Chemistry, 1987, vol. 262(17), pp. 8128-8130.
Fologea et al, "Detecting single stranded DNA with a solid state nanopore", Nano Letters, 2005, vol. 5(10), pp. 1905-1909.
Glorikian et al., "Microfluidics for IVDS—Smart consumable product development: implications for molecular diagnostics", DX Directions 2010, Spring, pp. 12-16.
Goldshtein et al., "A rapid direct fluorescent assay for cell-free DNA quantification in biological fluids", Annals of Clinical Biochemistry, 2009, vol. 46(Pt 6), pp. 488-494.
Gorkin et al., "Centrifugal microfluidics for biomedical applications", Lab on a Chip, 2010, vol. 10, pp. 1758-1773.
Gusev et al., "Capillary columns with in situ formed porous monolithic packing for micro high-performance liquid chromatography and capillary electrochromatography", Journal of Chromatography A, 1999, vol. 855(1), pp. 273-290.
Hatch et al., "Integrated preconcentration SDS-PAGE of proteins in microchips using photopatterned cross-linked polyacrylamide gels", Analytical Chemistry, 2006, vol. 78(14), pp. 4976-4984.
Heraeus, "Infrared emitters for industrial processes", Heraeus Noblelight GmbH brochure No. 0915 HNG-B 30 E 5C, pp. 1-16.
Heraeus, "New generation: short carbon infrared emitters", Heraeus Noblelight GmbH data sheet, Jan. 2015, 1 p.
Herr et al., "Microfluidic immunoassays as rapid saliva-based clinical diagnostics", Proceedings of the National Academy of Science USA, 2007, vol. 104(13), pp. 5268-5273.
Herr et al., "On-chip coupling of isoelectric focusing and free solution electrophoresis for multidimensional separations", Analytical Chemistry, 2003, vol. 75(5), pp. 1180-1187.
Holmberg et al., "Depurination of A4256 in 28 S rRNA by the ribosome-inactivating proteins from barley and ricin results in different ribosome conformations", Journal of Molecular Biology, 1996, vol. 259(1), pp. 81-94.
Holmes et al., "Leukocyte analysis and differentiation using high speed microfluidic single cell impedance cytometry", Lab on a Chip, 2009, vol. 9, pp. 2881-2889.
Huang et al., "The primary structure of *Staphylococcal enterotoxin* B: III. The cyanogen bromide peptides of reduced and aminoethylated enterotoxin B, and the complete amino acid sequence", Journal of Biological Chemistry, 1970, vol. 245(14), pp. 3518-3525.

Huang et al., "Microfabrication of a tapered channel for isoelectric focusing with thermally generated pH gradient", Electrophoresis, 2002, vol. 23(20), pp. 3504-3510.

IVD Technology, "Microfluidic applications for IVDs", DX Directions, 2010, Spring, pp. 6.

Kim et al., "Fully integrated lab-on-a-disc for nucleic acid analysis of food-borne pathogens", Analytical Chemistry, 2014, vol. 86, pp. 3841-3848.

Koh et al., "Centrifugal microfluidic platform for ultrasensitive detection of botulinum toxin", Analytical Chemistry, 2015, vol. 81, pp. 922-928.

Koh et al., "Centrifugal microfluidic platform for integrated analysis of proteins and nucleic acids from clinical and environmental samples", Sandia Report SAND2016-4449A, microTAS 2016, held on Oct. 9-13, 2016 in Dublin, Ireland (2 pp.).

Lee et al., "Fully integrated lab-on-a-disc for simultaneous analysis of biochemistry and immunoassay from whole blood", Lab on a Chip, 2011, vol. 11(1), pp. 70-78.

Lee et al., "A fully automated immunoassay from whole blood on a disc", Lab on a Chip, 2009, vol. 9(11), pp. 1548-1555.

Lim et al., "Bead-based microfluidic immunoassays: The next generation", Biosensors and Bioelectronics, 2007, vol. 22(7), pp. 1197-1204.

Lim et al., "Rapid isoelectric trapping in a micropreparative-scale multicompartment electrolyzer", Electrophoresis, 2007, vol. 28(12), pp. 1851-1859.

Lo et al., "Photopolymerized diffusion-defined polyacrylamide gradient gels for on-chip protein sizing", Lab on a Chip, 2008, vol. 8(8), pp. 1273-1279.

Lo et al., "Plasma DNA as a prognostic marker in trauma patients", Clinical Chemistry, 2000, vol. 46(3), pp. 319-323.

Long et al., "Integration of nanoporous membranes for sample filtration/preconcentration in microchip electrophoresis", Electrophoresis, 2006, vol. 27(24), pp. 4927-4934.

Madou et al., "Lab on a CD", Annual Review of Biomedical Engineering, 2006, vol. 8, pp. 601-628.

Maes et al., "Comparison of sample fixation and the use of LDS-751 or anti-CD45 or leukocyte identification in mouse whole blood for flow cytometry", Journal of Immunological Methods, 2007, vol. 319(1-2), pp. 79-86.

Martinez-Duarte et al., "The integration of 3D carbon-electrode dielectrophoresis on a CD-like centrifugal microfluidic platform", Lab on a Chip, 2010, vol. 10, pp. 1030-1043.

McBain et al., "Polyethyleneimine functionalized iron oxide nanoparticles as agents for DNA delivery and transfection", Journal of Material Chemistry, 2007, vol. 17(24), pp. 2561-2565.

Melting Temperature Calculation. Retrieved on asf from the internet: http://www.biophp.org/minitools/melting_temperature/demo.php?primer-CGT+TAC+CCG+CAG&basic-1&NearestNeighbor=1&cp=200&cs=50&cmg=0.

Min et al., "Functional integration of DNA purification and concentration into a real time micro-PCR chip", Lab on a Chip, 2011, vol. 11(2), pp. 259-265.

Phaneuf et al., "Portable centrifugal microfluidic platform for nucleic acid detection", SAND Report SAND2016-4452A, 20th International Conference on Miniaturized Systems for Chemistry and Life Sciences, held on Oct. 9-13, 2016 in Dublin, Ireland (2 pp.).

Phaneuf et al., "Portable centrifugal microfluidic platform for nucleic acid detection", SAND Report SAND2016-7047C, 20th International Conference on Miniaturized Systems for Chemistry and Life Sciences, held on Oct. 9-13, 2016 in Dublin, Ireland (2 pp.).

Phaneuf et al., "Portable centrifugal microfluidic platform for nucleic acid detection", SAND Report SAND2016-10698C, 20th International Conference on Miniaturized Systems for Chemistry and Life Sciences, held on Oct. 9-13, 2016 in Dublin, Ireland (1 p.).

Phaneuf et al., "Non-contact heating system for a centrifugal microfluidic platform", SAND Report SAND2015-8608C, Proposed for presentation at the Lab-on-a-Chip, Microfluidics & Microarrays World Congress, held on Sep. 28-30, 2015 in San Diego, CA, 1 p.

Phaneuf et al., "Non-contact heating system for a centrifugal microfluidic platform", SAND Report SAND2015-3786A, 19th International Conference on Miniaturized Systems for Chemistry and Life Sciences, held on Oct. 25-29, 2015 in Gyeongju, South Korea (2 pp.).

Phaneuf et al., "Rapid, portable, multiplexed detection of bacterial pathogens directly from clinical sample matrices", Biosensors, 2016, vol. 6, article 49 (10 pp.).

Phaneuf et al., "Portable centrifugal microfluidic system for diagnostics in resource-limited settings", 2016 IEEE Healthcare Innovation Point-of-Care Technologies Conference (HI-POCT), held on Nov. 9-11, 2016 in Cancun, Mexico (3 pp.).

Price et al., "Light-scattering immunoassay", in Principles and Practice Immunoassay (Second Ed., C.P. Price & D.J. Newman, eds.), 1997, Stockton Press (New York, NY), Chap. 18, pp. 446-481.

Rhodes et al., "Plasma DNA concentration as a predictor of mortality and sepsis in critically ill patients", Critical Care, 2006, vol. 10(2), Article R60 (pp. 1-7).

(56) References Cited

OTHER PUBLICATIONS

Riahi et al., "Molecular detection of bacterial pathogens using microparticle enhanced double-stranded DNA probes", Analytical Chemisty, 2011, vol. 83(16), pp. 6349-6354 and Supporting Information (8 pp.).

Rider et al., "A B cell-based sensor for rapid identification of pathogens", Science, 2003, vol. 301, pp. 213-215.

Riegger et al., "Read-out concepts for multiplexed bead-based fluorescence immunoassays on centrifugal microfluidic platforms", Sensors and Actuators A-Physical, 2006, vol. 126, pp. 455-462.

Roy et al., "From cellular lysis to microarray detection, an integrated thermoplastic elastomer (TPE) point of care lab on a disc", Lab on a Chip, 2015, vol. 15, pp. 406-416.

Saukkonen et al., "Cell-free plasma DNA as a predictor of outcome in severe sepsis and septic shock", Clinical Chemistry, 2008, vol. 54(6), pp. 1000-1007.

Schaff et al., "Differential white cell count by centrifugal microfluidics", microTAS 2010 Conference, held on Oct. 3-7, 2010 in Groningen, The Netherlands (1 p.).

Schaff et al., "Whole blood immunoassay based on centrifugal bead sedimentation", Clinical Chemistry, 2011, vol. 57(5), pp. 753-761.

Schembri et al., "Portable simultaneous multiple analyte whole-blood analyzer for point-of-care testing", Clinical Chemistry, 1992, vol. 38(9), pp. 1665-1670.

Schneider et al., "Characterization of EBV-genome negative "null" and "t" cell lines derived from children with acute lymphoblastic leukemia and leukemic transformed non-Hodgkin lymphoma", International Journal of Cancer, 1977, vol. 19(5), pp. 621-626.

Sommer et al., "On-chip isoelectric focusing using photopolymerized immobilized pH gradients", Analytical Chemistry, 2008, vol. 80(9), pp. 3327-3333.

Suzuki et al., "Experimental optimization of probe length to increase the sequence specificity of high-density oligonucleotide microarrays", BMC Genomics, 2007, vol. 8, Art. 373 (13 pp.).

Tan et al., "Miniaturized capillary isoelectric focusing in plastic microfluidic devices", Electrophoresis, 2002, vol. 23(20), pp. 3638-3645.

Yu et al., "Bioinformatic processing to identify single nucleotide polymorphism that potentially affect Ape1 function", Mutation Research/Genetic Toxicology and Environmental Mutagenesis, 2011, vol. 722(2), pp. 140-146.

Zhang et al., "A new biodosimetric method: branched DNA-based quantitative detection of B1 DNA in mouse plasma", British Journal of Radiology, 2010, vol. 83, pp. 694-701.

Ziegler et al., "Circulating DNA: a new diagnostic gold mine?", Cancer Treatment Reviews, 2002, vol. 28, pp. 255-271.

Zilberstein et al., "Parallel isoelectric focusing chip", Proteomics, 2004, vol. 4(9), pp. 2533-2540.

Zilberstein et al., "Parallel isoelectric focusing II", Electrophoresis, 2004, vol. 25(21-22), pp. 3643-3651.

Zilberstein et al., "Parallel processing in the isoelectric focusing chip", Electrophoresis, 2003, vol. 24(21), pp. 3735-3744.

Zuo et al., "A method for global analysis of complex proteomes using sample prefractionation by solution isoelectrofocusing prior to two-dimensional electrophoresis", Analytical Biochemisty, 2000, vol. 284(2), pp. 266-278.

\* cited by examiner

NON-CONTACT TEMPERATURE CONTROL SYSTEM FOR MICROFLUIDIC DEVICES

CROSS-REFERENCE TO RELATED APPLICATION

This application claims the benefit of U.S. Provisional Application No. 62/370,843, filed Aug. 4, 2016, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to a temperature control system for a microfluidic device. The system allows for non-contact heating by employing an infrared emitter. In some instances, the system can be used in conjunction with a centrifugal microfluidic device. Optionally, a mask can be implemented to provide selective heating of desired assay areas of the device.

BACKGROUND OF THE INVENTION

For microfluidic systems, temperature control can provide enhanced modalities to control reaction rates, as well as to perform certain amplification reactions. Traditionally, contact-based heaters (e.g., resistive or thermoelectric heaters) are employed with such systems. These contact-based heaters can provide efficient heating in a simple manner. However, complications can arise when integrating such heaters with centrifugal microfluidic systems. Due to the required rotational motion of the microfluidic device, a slip ring (or similar interface) may be required to maintaining electrical contact between the heater and the rotating device. Such slip ring structures can complicate the design, have limited lifetimes due to brush contact wear, and limit the maximum operating speed. Accordingly, there is a need for other heating systems capable of providing a simplified interface with a rotating device while efficiently controlling temperature.

SUMMARY OF THE INVENTION

The present invention relates to a non-contact temperature control system for use with a microfluidic device. The system employs an infrared emitter to direct radiation to a surface of the device. Various other components can be employed to increase heating efficiency (e.g., by employing a reflector to reflect radiation back to the heated surface), to provide selective heating of a particular portion of the device (e.g., by employing a mask, as described herein), and/or to cool the heating element (e.g., by employing a cooling fan). The system can include other modules to rotate the device and/or to detect one or more targets within an assay area of the idea. The present invention also encompasses an integrated system, in which various enclosures can be configured to house the components and the enclosures themselves are configured to provide a contained system.

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

The present invention relates to a non-contact temperature control system for a microfluidic device (e.g., a microfluidic disc). In particular, the system employs an infrared emitter to provide non-contact heating, which can be especially useful when employed with a device configured to be rotated (e.g., as in a centrifugal device) and/or configured to perform centrifugal sedimentation-based assays. Optionally, the system can include other modules (e.g., a motor module, a detection module, and/or a processing device) to facilitate use of the microfluidic device to perform any useful analysis or assay (e.g., any described herein).

Figure 1A:
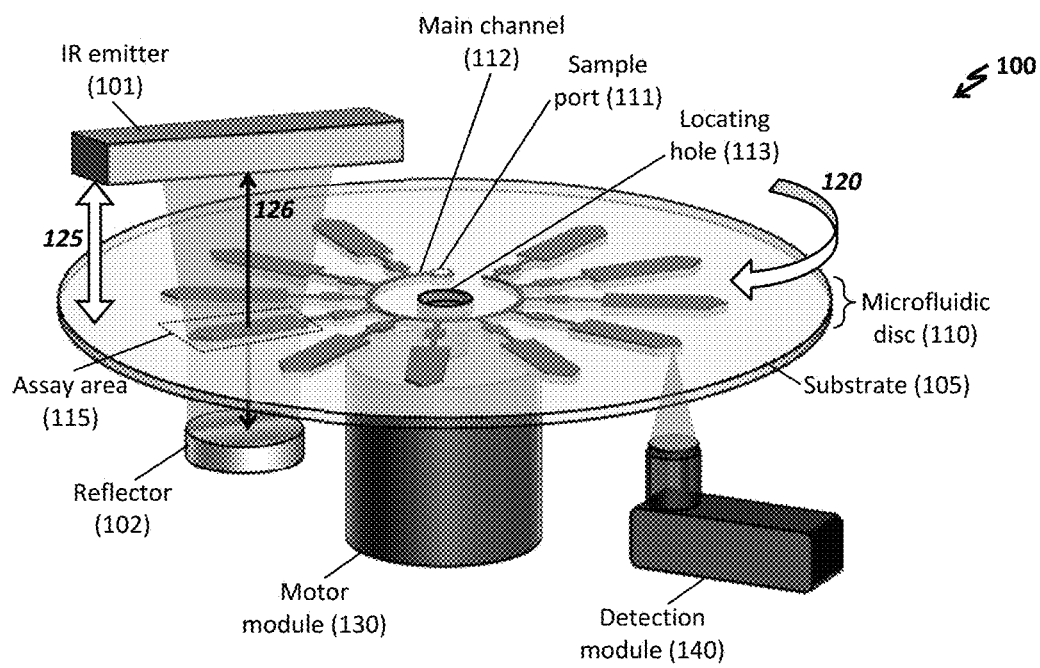
FIG. 1A-1B shows an exemplary non-contact temperature control system for a microfluidic device. Provided is a schematic of an exemplary system 100 including an infrared emitter 101 (FIG. 1A). Also provided is a thermal image of the top surface of the heated disc provided a reference point for temperature monitoring (FIG. 1B), in which region 1 overlies the assay areas of the disc.

FIG. 1A provides an exemplary non-contact temperature control system 100 for a microfluidic device. As can be seen, the system includes an infrared emitter 101 and a reflector 102 configured to reflect radiation. The emitter and reflector can be positioned, relative to the microfluidic device (e.g., a microfluidic disc 110), in any useful manner. In one instance, the emitter 101 is positioned to direct radiation to a first surface (e.g., a top surface) of the microfluidic disc 110, and the reflector 102 is positioned to collect radiation from a second surface (e.g., a bottom surface) of the microfluidic disc 110, where the second surface opposes the first surface. In addition, the focal point of the emitter can configured to be positioned on or within an assay area 115, or a portion thereof. The emitter can be configured to emit any useful wavelength, e.g., such as a wavelength of from about 1 µm to about 5 µm (e.g., from 1 µm to 4 µm, 1 µm to 3 µm, 2 µm to 5 µm, 2 µm to 4 µm, or 2 µm to 3 µm).

Figure 1B:
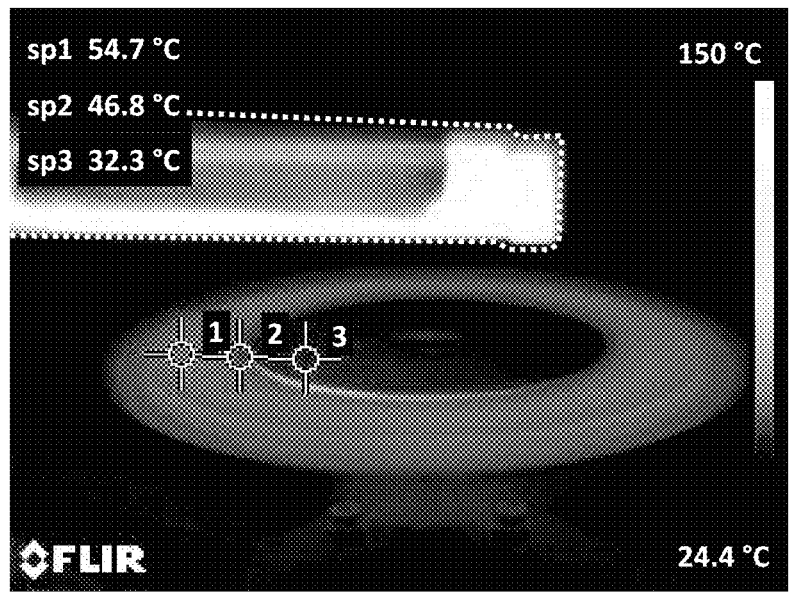

The positions of the emitter and reflector can be aligned along any useful axis. In one instance, the focal point of the emitter 101 and a vertex of the reflector 102 are aligned along a central axis 126. In another instance, the distance 125 between the emitter and the focal point of the emitter can be optimized to provide uniform heating and/or the desired heating temperature. In yet another instance, the emitter is positioned above the assay area of the microfluidic device. As seen in FIG. 1B, position 1 corresponds to a position above the assay area of the device, positions 2 and 3 correspond to positions located towards the center of the device.

The microfluidic device can have any useful structural features. In one instance, the device is a microfluidic disc 110 having a plurality of assay areas 115 disposed within or upon the substrate 105. Each assay area 115 can be in fluidic communication with a sample port 111 configured to provide a sample (e.g., a fluid sample) or a portion thereof (e.g., a fraction or a particular volume of the sample) to the assay area. Fluidic communication can include the use of a main channel 112 connecting the sample port 111 directly or indirectly to an assay area 115. Indirect fluidic communication can include the use of intervening chamber(s) or valve(s) of any useful geometry or fluidic connection (e.g., any chamber described herein, such as reservoirs, channels, etc.). The disc 110 can further include any useful structure, such as a locating hole 113 or a tooth element, to interact with the motor module 130 configured to rotate 120 the disc 110.

Modules can be positioned to ensure efficient and/or effective heating of the disc. In one embodiment, the emitter is positioned opposite of the reflector. In another embodiment, as seen in FIG. 1A, the motor module 130 and the detection module 140 are positioned opposite of the emitter 101 (e.g., on opposing sides of the disc 110) to reduce thermal damage to the motor and/or detection components. In addition, the emitter and the detection module can be positioned on opposing lateral sides. As seen in FIG. 1A, the emitter 101 is positioned on one lateral side of the disc 110, and the detection module 140 is positioned on the opposing lateral side of the emitter 101.

Figure 2A:
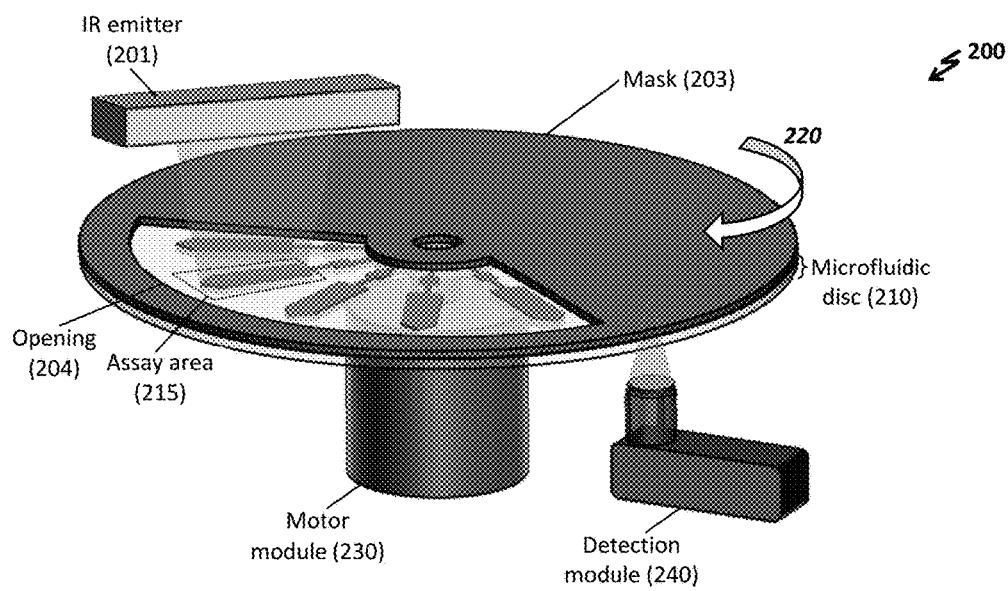
FIG. 2A-2B shows another exemplary non-contact temperature control system. Provided are schematics of an exemplary system 200 including a mask 203 (FIG. 2A) and a disc 210 having a plurality of assay areas 215 labeled A1 to A11 (FIG. 2B).

The system can include one or more additional structural features to selectively heat portions of the device. As seen in FIG. 2A, the system 200 can include an infrared emitter 201 and a mask 203 (e.g., an optically opaque mask) configured to include an opening 204. By positioning the opening 204 above a particular assay area 215, that area is selectively heated by the emitter 201. The remaining shielded portions of the disc 210 will not be heated. If the mask 203 is configured to rotate with the disc 210, then selective heating can be maintained during rotation 220 by the motor module 230. The mask 203 can be provided to be in proximity to a first surface (e.g., the top surface) of the disc 210, and the detection module 240 can be provided to be in proximity to a second surface (e.g., the bottom surface) of the disc 210, in which the second surface opposes the first surface. In this way, the mask will not interfere with the detection signal to be detected by the detection module.

Figure 2B:
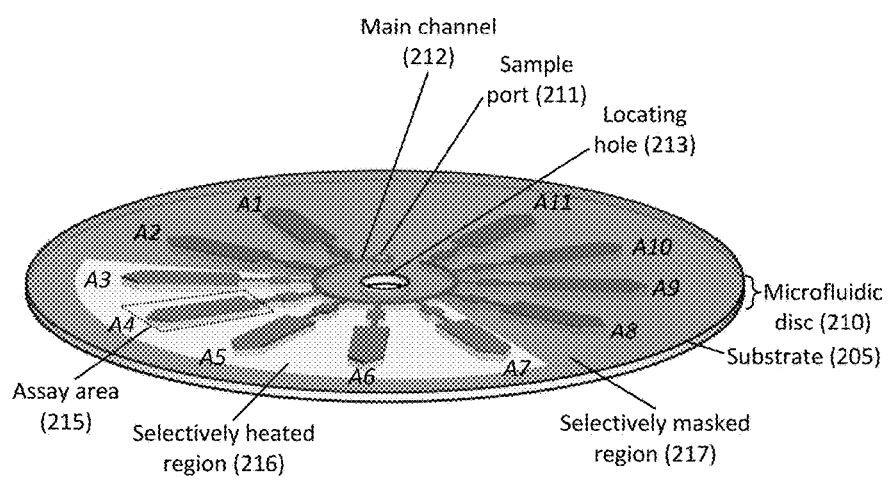

The mask can be further configured to provide selective heating of any portion of the disc. As seen in FIG. 2B, the mask can be configured to provide an opening that defines the selectively heated region 216 of the substrate 205 and to provide a shielded portion that defines the selectively masked region 217 of the substrate 205. Any useful number of assay areas 215 can be exposed within the opening. As seen in FIG. 2B, assay areas A3-A7 are exposed within the opening, thus these areas constitute the selectively heated region 216. Other assay areas A1, A2, A8-A11 are shielded and will not be heated by the focal point of the emitter.

The mask can include one or more openings, which can be provided in any useful spatial pattern to provide selective heating of any useful portion of the microfluidic disc. In addition, the mask can include any useful shielded portion to protect any portion of the disc from extensive heating. In one embodiment, the mask can include shielded regions over the main channel 212 and/or the sample port 211 to reduce excessive heating of the sample, which can result in fluid leakage, pressure build-up, and/or sample deactivation. The mask can also include an alignment hole that aligns with the locating hole 213 of the disc 210, so that the mask and the disc can be aligned together and rotated along a central rotational axis of the motor module.

Figure 3A:
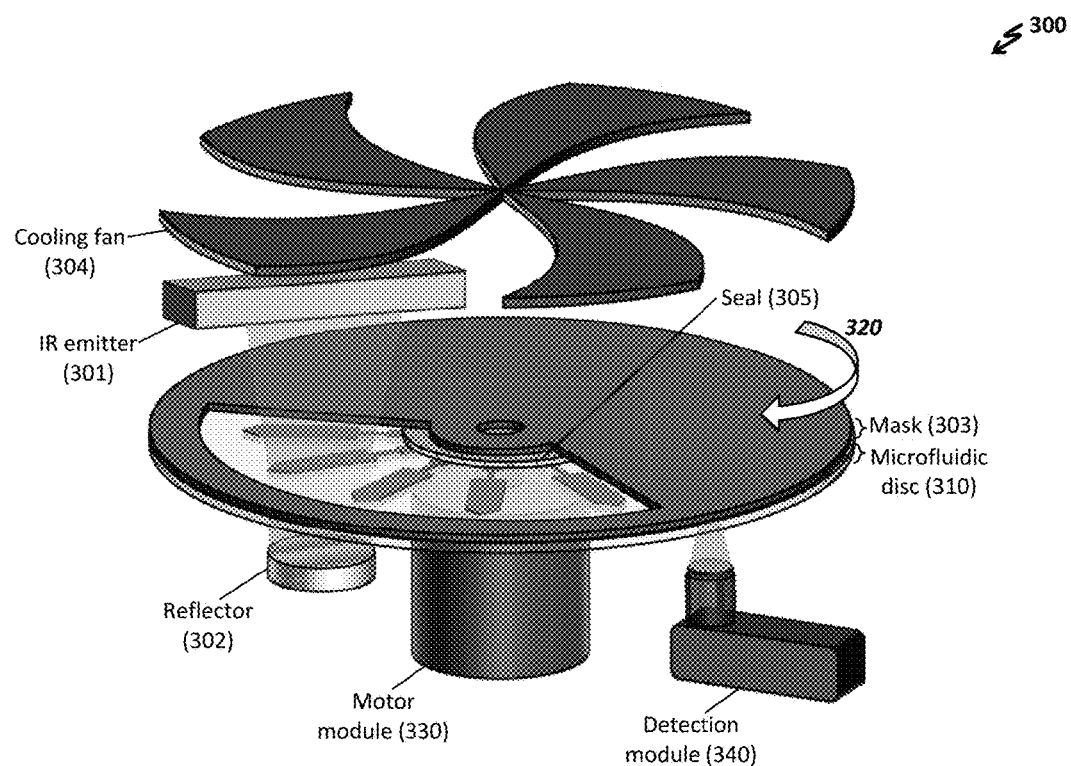
FIG. 3A-3C shows yet another exemplary non-contact temperature control system. Provided are schematics of an exemplary system 300 including a cooling fan 304 (FIG. 3A), another exemplary system 3000 provided within an upper enclosure 3010 and a lower enclosure 3015 (FIG. 3B), and yet another exemplary system 3100 provided within a hinged system having an upper enclosure 3110 and a lower enclosure 3115 (FIG. 3C).

The system may include other structural elements for use with the emitter. As seen in FIG. 3A, the system 300 can include a cooling fan 304 configured to be in proximity to the emitter 301. The system can also include a mask 303 to provide selective heating of assay areas, as well as a seal 305 disposed upon the microfluidic disc to minimize heating of portions of the microfluidic disc 310 that is not an assay area (e.g., minimize heating in proximity to the sample port and/or main channel). Further, the system can include a reflector 302 (e.g., as described herein). A motor module 330 can be configured to be coupled to the microfluidic disc 310 and to spin 320 the microfluidic disc in response to a motor control signal; and a detection module 340 can be configured to detect a signal from one or more label agents present in the assay area.

Figure 3B:
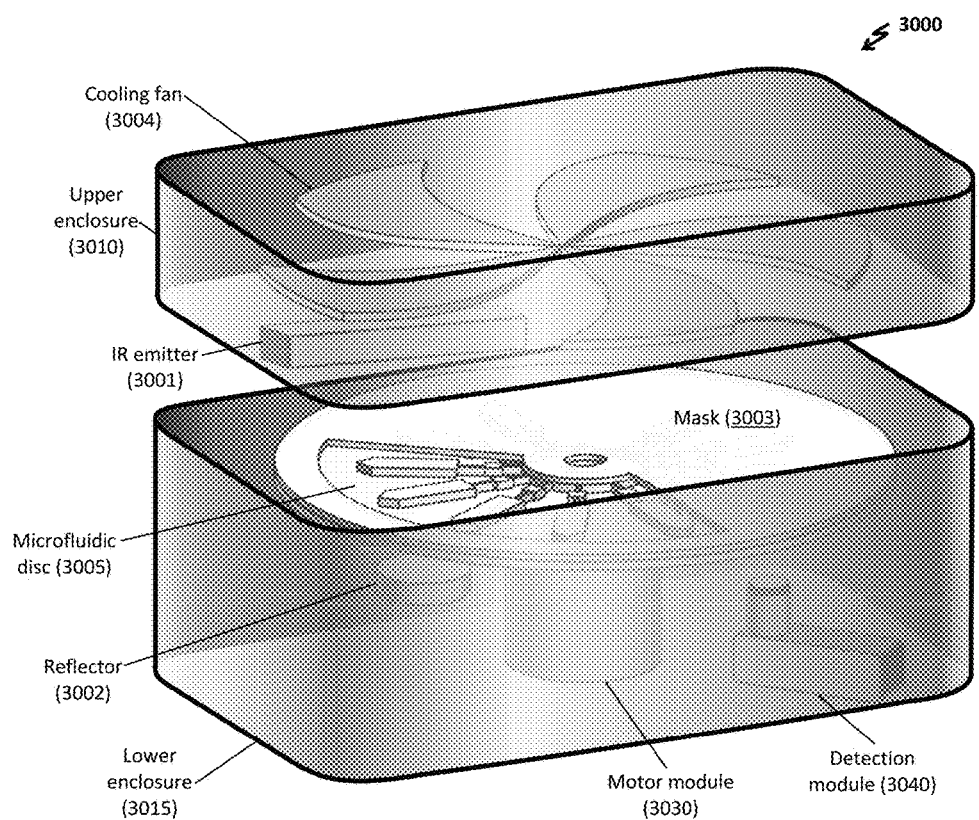

The system can be provided in any useful enclosure. As seen in FIG. 3B, the system 3000 can include an emitter 3001 and a cooling fan 3004 disposed in an upper enclosure 3010, which in turn is configured to close over a lower enclosure 3015. The lower enclosure 3015 can include the remaining components and modules, which are configured to be aligned with the emitter when the upper and lower enclosures are mated. The lower enclosure 3015 can include a motor module 3030 configured to provide an aligned microfluidic disc 3005 (e.g., as determined by the position of the focal point of the emitter, which can be configured to be positioned on or within an assay area, or a portion thereof, of the microfluidic disc 3005); a detection module 3040; and an aligned reflector 3002 (e.g., configured to reflect radiation that is collected from a second surface of the microfluidic disc 3005, where the second surface opposes the first surface at which the emitter is positioned to direct radiation, and/or where the focal point of the emitter and a vertex of the reflector are aligned along a central axis). An optional mask 3003 can be housed in the lower enclosure 3015.

Figure 3C:
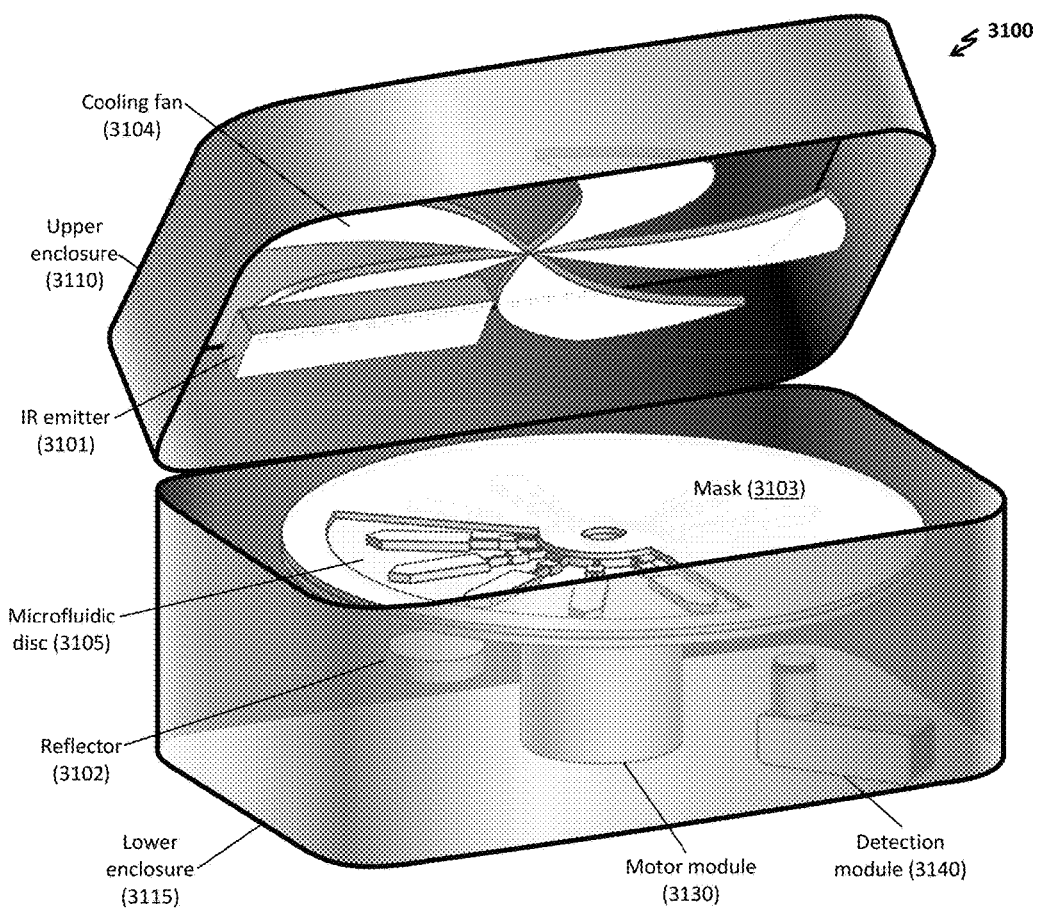

The upper and lower enclosures can interact in any useful manner. In one instance, the upper enclosure has an edge that mates with the edge of the lower enclosure (e.g., as in FIG. 3B). In another instance, the upper enclosure and lower enclosure are connected by way of a hinge (e.g., as in FIG. 3C). FIG. 3C provides a system 3100 including an emitter 3101 and a cooling fan 3104 disposed in an upper enclosure 3110, which in turn is configured to close over a lower enclosure 3015; a hinge disposed between the upper enclosure 3110 and the lower enclosure 3115; and a microfluidic disc 3105, an optional mask 3103, an aligned reflector 3102, a motor module 3130, and a detection module 3140 disposed in the lower enclosure 3115. Additional exemplary systems are provided in FIGS. 4A-4D and FIGS. 5A-5B.

Centrifugal Devices

A microfluidic disc can be operated as a centrifugal device. In some instances, the device includes a substrate that may at least partially define an assay region, as well as a port (e.g., a sample port or inlet port) configured to receive a sample. The port can be in fluidic communication with any useful chamber (e.g., within an assay area) or any useful region of the device (e.g., an assay area). During operation, a sample (e.g., a fluid sample including a plurality of particles, such as beads or cells) may be transported by applying a centrifugal force that is directed from an interior of the microfluidic disc toward a periphery of the microfluidic disc. The centrifugal force may be generated by rotating the microfluidic disc in any useful direction.

The device can be designed to facilitate multiplexed detection, in which multiple samples can be processed at the same time and/or each particular sample can be divided to be tested for multiple different targets. For instance, the device can include a plurality of assay areas configured for multiplexed and/or parallel detection.

Assay Areas, Including Detection Regions

An assay area includes any portion defined in part by a substrate, in which the assay area facilitates one or more reaction(s), separation(s), and/or detection of a desired target. The assay area can be defined by one or more chambers (e.g., a reagent chamber, an assay chamber, an incubation chamber, as well as channels connecting any useful chamber) in fluidic communication with a sample port configured to receive a test sample. The assay area can include a detection region, which can be a chamber (e.g., a channel) configured to allow for detection of a signal emitted by a label agent that can optionally be affixed directly or indirectly to the target and/or a particle (e.g., a bead or a cell).

During operation, a centrifugal force may generally be used to transport a fluid sample (optionally including particles) from an inlet port (e.g., a sample port) toward an assay area (e.g., a detection region of the assay region). Additionally, centrifugal forces may be used to transport density medium and/or particles from one or more reservoir(s) to the assay area.

The density medium can have a density greater than that of the fluid sample but lower than that of the particles to be detected. These differences in density can be employed to separate the particles from the fluid sample. By applying centrifugal force, flows are induced. Denser particles from the fluid sample are transported through the density medium, but the less dense components of the fluid sample are not transported through the density medium. In this manner, the particles (e.g., bound to one or more targets) are selectively separated from the remaining portions of the test sample, and detection limits can display improved sensitivity and/or selectivity.

The assay area can include a narrowed or tapered region, which can facilitate detection within the assay area. For instance, upon providing a centrifugal force, a sedimentation-based assay can be conducted within the assay area, such that a pellet is formed in a portion of the assay area closest to the edge of the microfluidic device. If this portion terminates in a narrowed or tapered region, then the pellet is distributed across a larger surface area, which may be more effective at transmitting a detection signal. In one instance, a fluorescence signal can be more easily detected across this narrowed region due to reduced scattering, thereby increasing the sensitivity of the assay. Accordingly, the assay area can have any useful dimension (e.g., width, height, radius, depth, etc.) and/or cross-section (e.g., rectangular, triangular, semi-circular, rounded, trapezoidal, etc.) that can be uniform or non-uniform along any axis or dimension. Further details on narrowed or tapered regions are described in U.S. Pat. No. 8,962,346, which is incorporated herein by reference in its entirety.

Chambers

The present apparatus (e.g., device, such as a microfluidic disc) can include one or more chambers, which can be configured to substantially enclose a fluid or a substance in the fluidic device (e.g., a microfluidic disc). Such chambers can include one or more ports (e.g., inlets or outlets), fluidic opening (e.g., vias), fluidic barriers, channels, or any other structure to allow for fluidic communication between one or more chambers, vents, etc. Exemplary chambers include a channel, a reservoir, etc., having any useful geometry or dimension.

The chambers can be designated for a particular use. Particular uses for such chambers include a sample chamber for receiving and/or storing a test sample, an incubation chamber for incubating a test sample, a reaction chamber for reacting a test sample or a processed sample with another reagent, a reagent chamber containing one or more reagents for detecting one or more targets (e.g., containing one or more label agents), a sterilization chamber containing one or more reagents to sterilize or disinfect the test sample (e.g., containing one or more sterilization agents, as described herein), an assay chamber for conducting one or more assays to detect one or more targets, a post-processing chamber to perform one or more procedures (e.g., lysis, polymerase chain reaction (PCR), amplification assay, immunoassay, analytic test, and/or biochemical analysis), and/or a waste chamber for storing one or more by-products of the assay. Each of these chambers can be interconnected by a valve (e.g., a passive valve, an active valve, an NC valve, and/or NO valve) and/or a channel that can optionally include such a valve in its fluidic path.

Substances and materials within a chamber can be transported to any other chamber in any useful manner. In one instance, rotation over a certain threshold results in transporting a reagent from a first chamber to another chamber (e.g., from a reservoir to a chamber in the assay area; or from a sample port to a reservoir; or from a sample port to a chamber in the assay area). In other instances, a channel can have a dimension that requires a certain rotation rate to overcome capillary pressure, such that the channel functions as a valve. In other instances, the channel includes a wax-based valve that requires melting for actuation. Other methods of controlling flow in microfluidic devices (e.g., pressure-induced flow, centrifugal force-driven flow, pumping, etc.) are known and can be implemented with the devices and systems herein.

Microfluidic Devices and Systems

An exemplary system can include one or more modules or components to facilitate performing assays with the microfluidic disc. In one non-limiting instance, the system includes a microfluidic disc, a motor module coupled to the disc and configured to spin the disc in order to generate centrifugal forces, a detection module positioned to detect a signal from one or more label agents in the assay area (e.g., within a detection region), and an optional processing device. An optional actuator may be coupled to the detection module and configured to move the detection module along the detection region in some examples.

In one instance, the motor module may be implemented using a centrifugation and/or stepper motor. The motor module may be positioned relative to the detection module, such that placing the disc on the motor ensures that an assay area, or a portion thereof, is exposed to the detection module. The motor module can include any useful motor, e.g., a brushed DC motor, a solenoid, a servo motor, a linear actuator, as well as combinations thereof, and a controller (e.g., a motor controller).

The detection module may include a detector (e.g., an electronic detector, an optical detector, a cell phone camera, a photodiode, a photomultiplier tube, and/or a CCD camera) suitable for detecting a signal from one or more label agents (e.g., affixed to particles to be detected and/or quantified). The detector module may include, for example, a laser and optics suitable for optical detection of fluorescence from fluorescent labels. In other examples, other detectors, such as electronic detectors, may be used. An optional actuator may move the detector to a variety of locations of the microfluidic disc (e.g., along the assay area) to detect a measurable signal. The one or more actuators may be coupled to the motor module and/or disc, such that the disc is moved relative to the detection module in response to signals from the processing device.

A processing device may be coupled to the motor module, the detection module, and/or the actuator. Furthermore, the processing device can be configured to provide one or more signals (e.g., one or more control signals to those modules and/or components), as well as to receive one or more signals (e.g., one or more electronic signals from the detection module corresponding to the presence or absence of label agent). All or selected components or modules may be housed in a common housing or in separate enclosures (e.g., optionally configured to operate together, such as by providing a hinged housing formed by connecting an upper enclosure to a lower enclosure by use of a hinge). The processing device can include any useful circuitry, control boards, switches (e.g., optical switches), power supply, input hubs, output hubs, etc. Microfluidic discs may be placed on the motor module and removed, such that multiple discs may be analyzed by the system.

The processing device may include one or more processing units, such as one or more processors. In some examples, the processing device may include a controller, logic circuitry, and/or software for performing functionalities described herein. The processing device may be coupled to one or more memories, input devices, and/or output devices including, but not limited to, disc drives, keyboards, mice, and displays. The processing device may provide control signals to the motor module to rotate the microfluidic disc at selected speeds for selected times. The processing device may provide control signals to the detection module (e.g., including one or more detectors and/or actuators), detect signals from the label agent(s), and/or move the detector to particular locations. The processing device may develop these control signals in accordance with input from an operator and/or in accordance with software. The software may include one or more executable instructions (e.g., stored on one or more memories) configured to cause the processing device to output a predetermined sequence of control signals, to perform one or more calculations (e.g., determine the presence or absence of a target based on electronic signals from the detection module), to communicate any useful output (e.g., a result, a setpoint, a level, etc.) over a network, to store any useful output in memory, and/or display any useful output on a display module. It is to be understood that the configuration of the processing device and related components is quite flexible, and any of a variety of computing systems may be used including server systems, desktops, laptops, controllers, and the like.

The system can include any other modifications to facilitate rotation of the device and/or detection within the device. In one instance, the device includes a structure configured to align an assay area with a detection module. In one non-limiting embodiment, an assay area can include a corresponding tooth element. In another non-limiting embodiment, each assay area includes a corresponding tooth element. In yet another non-limiting embodiment, one tooth element can be an extended tooth element having a different dimension than another tooth element. In use, the system can include a device including a plurality of assay regions and corresponding tooth elements; a motor module configured to move the device such that the assay areas move along a first path (e.g., a circular path disposed on a surface of the device) and the tooth elements move along a second path (e.g., a circular path disposed on an edge or along a periphery of the device); an impinging element configured for placement in a first position that allows for movement of device and a second position, wherein the impinging element engages at least one tooth element when in the second position; a detection module configured to detect a signal (e.g., arising the detection region or the assay area; arising from one or more label agents or one or more targets); and processing device (e.g., a controller) communicatively coupled to the impinging element and the motor module, where the processing device is configured to provide a control signal to the impinging element to place the impinging element in the first position or the second position. In some embodiments, the detection module is positioned such that when the impinging element is in the second position, the detection module is aligned with at least one of the plurality of assay regions.

Exemplary devices (e.g., apparatuses) and systems, as well as methods employing such devices and systems, are described in U.S. Pat. Nos. 8,945,914 and 9,186,668, as well as U.S. Pat. Appl. Pub. No. 2015/0360225, each of which is incorporated herein by reference in its entirety.

Density Medium and Particles

The present invention can be employed with any useful agents, including a density medium, a particles, as well as combinations thereof. The density medium may have a density lower than a density of a plurality of particles (e.g., beads or cells) and higher than a density of the fluid sample. The density medium may generally be implemented using a fluid having a density selected to be in the appropriate range, e.g., lower than a density of the particles to be detected or quantified and higher than a density of the fluid sample. In some examples, a fluid sample may be diluted for use with a particular density medium. The density medium may include, for example, a salt solution containing a suspension of silica particles, which may be coated with a biocompatible coating (e.g., a polyvinylpyrrolidone (PVP) coating or a silane coating). Examples of suitable density media are Percoll™ (colloidal silica coated with PVP), Percoll™ PLUS (colloidal silica coated with silane), Ficoll™ PM70 (high molecular weight sucrose-polymers with an average molecular weight of 70,000), Ficoll™ PM400 (a synthetic neutral, highly-branched hydrophilic polymer of sucrose with an average molecular weight of 400,000), Ficoll-Paque™ PLUS (a combination of Ficoll™ PM400, sodium diatrizoate, and disodium calcium EDTA), and Ficoll-Paque™ Premium (a combination of Ficoll™ PM400, sodium diatrizoate, and disodium calcium EDTA in water for injection), each of which is available from GE Healthcare Life Sciences, Little Chalfont, Buckinghamshire, United Kingdom. Particular densities may be achieved by adjusting a percentage of the density medium in a salt solution. Generally, viscosity and density of the density medium may be adjusted by selecting a composition of the medium. Varying the concentration of solutes such as sucrose or dextran in the medium may adjust the density and/or viscosity.

In some instances, sedimentation assays can be conducted, in which the settling velocity of a particle is described by known Stoke's flow equations. Sedimentation rates typically scale with a square of a particle's radius and can be linearly dependent with the difference in density between a particle and a surrounding fluid (e.g., as provided by a sample or by a density medium). Thus, under certain conditions, a population of particles can be separated according to its density and/or radius.

Particles of different sizes can be employed, in which the different sedimentation rates can be used to allow size-based separation and/or detection. The sedimentation rate of a particle is dependent on various characteristics of the particle, including particle size, particle surface charge, and/or particle density. Sedimentation can occur under any force, such as gravitational force or centrifugal force (e.g., by rotating or spinning a microfluidic device). In one non-limiting example, a first population of particles (e.g., having a first particle size and/or first particle density) can include a first type of capture agent, and a second population of particles (e.g., having a second particle size and/or second particle density) can include a second type of capture agent, thereby allowing for different sedimentation rates and/or separation zones for each population. For instance, smaller and/or less dense particles can be localized in a first separation zone, and larger and/or more dense particles can be localized in a second separation zone, thereby allowing for separation of different populations of particles by employing centrifugal force. Further details on sedimentation assays are provided in U.S. Pat. No. 8,945,914, which is incorporated herein by reference in its entirety.

Particles can be composed of any useful material and have any useful chemical properties (e.g., surface charge, including a positively charged surface or a negatively charged surface). Exemplary materials include polystyrene, polymethylmethacrylate, silica, metal (e.g., gold, iron, or iron oxide), as well as combinations thereof and coated versions thereof (e.g., including a polymer coating, a charged coating, or a coating including binding groups, such reactive linkers, antibodies, integrins, and/or selectins). Particles can have any useful dimension (e.g., as in microparticles, nanoparticles, etc.) depending on their use. For example, particle dimensions may be useful for use as sedimentation particles, whereas other dimensions or characteristics for use as labeling particles. In one non-limiting instance, a sedimentation particle can be modified to bind to certain cells, thereby increasing the sedimentation rate of certain cells upon binding and allowing these certain cell types to be selectively removed from the sample during centrifugation.

Other substances or reagents can be employed in conjunction with the density medium and/or a population of particles. In one instance, a separation layer fluid is employed, which forms an interface between a density medium and a sample, between a sample and a particle, and/or between the density medium and the particle. This separation layer fluid can have nay useful density (e.g., denser than the density medium but less dense than the particle; denser than the sample but less dense than the density medium; or denser than the sample but less dense than the particle). The separation layer fluid can include any useful substance, e.g., a hydrophobic material, a mineral oil, an organic oil, a charged or water ordering polymer, a salt in a water-based medium, a fluoroalkane fluid, a perfluorocarbon, or a perfluoroalkane fluid. Further details on separation layer fluids are provided in U.S. Pat. Nos. 8,962,346 and 9,304,129, each of which is incorporated herein by reference in its entirety.

Label Agents and Capture Agents

A label agent includes any moiety that can emit a signal suitable for detection, such as an optical or an electrical signal. The label agent can optionally include a capture portion, which binds to a target or a portion thereof. Furthermore, a label agent can be used in conjunction with a capture agent (e.g., as in a sandwich assay, which can include use of a capture agent to bind a first region of the target to a bead and use of a label agent to bind to a second region of the target in order to provide a detectable signal).

Exemplary capture agents include a protein that binds to or detects one or more markers (e.g., an antibody or an enzyme), an affibody, an aptamer, a globulin protein (e.g., bovine serum albumin), a nanoparticle, a microparticle, a sandwich assay reagent, a nucleic acid (e.g., single stranded nucleic acid, double stranded nucleic acid, hairpin nucleic acid, DNA, RNA, cell-free nucleic acids, as well as chimeras thereof, hybrids thereof, or modifications thereof), a toxin capture agent (e.g., a sarcin-ricin loop capture agent), a major histocompatibility complex capture agent (e.g., a MHC II capture agent), or a catalyst (e.g., that reacts with one or more markers.

Exemplary label agents include a capture agent (e.g., any herein), a detectable molecule or compound (e.g., a probe (e.g., a fluorescence resonance energy transfer or FRET probe, a fluorescent probe, and/or a quencher probe), an electroactive label, an electrocatalytic label, a fluorescent label, a colorimetric label, a quantum dot, a particle, a nanoparticle, a microparticle, a barcode, a radio label (e.g., an RF label or barcode), avidin, biotin, a tag, a dye, a marker, an enzyme that can optionally include one or more linking agents and/or one or more dyes, etc.), or a combination of a capture agent with a detectable molecule or a detectable compound. Other exemplary label agents include nucleic acid dyes, lipid dyes, etc.

Other Reagents

The present device can be configured for use with any number of reagents either on-chip and/or off-chip. Exemplary reagents include a lysing agent (e.g., a detergent, such as saponin); a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; an antibiotic; a catalyst; an enzyme; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, a coated particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer (e.g., for binding to a selective region of the target nucleic acid)), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a buffer (e.g., a phosphate or borate buffer, which can optionally include one or more salts, kosmotropes, and/or chaotropes), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

Samples

The sample can include any useful targets. Exemplary targets include cells (e.g., white blood cells, red blood cells, neutrophils, lymphocytes, monocytes, granulocytes, tumor cells, etc.), viruses, bacteria, and/or complexes. In any sample, a panel of targets can be present (e.g., a plurality of bacteria, pathogen(s), etc.).

Exemplary targets include a bacterium, such as such as *Bacillus* (e.g., *B. anthracis*), Enterobacteriaceae (e.g., *Salmonella, Escherichia coli*, Yersiniapestis, *Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii*, or *R. typhi*), *Francisella tularensis, Chlamydia psittaci, Coxiella burnetii, Mycoplasma* (e.g., *M. mycoides*), etc.; an allergen, such as peanut dust, mycotoxins, mold spores, or bacterial spores such as *Clostridium botulinum* and *C. perfringens*; a toxin, such as ricin, mycotoxin, tetrodotoxin, anthrax toxin, botulinum toxin, staphylococcal enterotoxin B, or saxitoxin; a virus, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acan-* thamoeba, *Entamoeba histolytica, Giardia lamblia, Trichomonas vaginalis, Leishmania,* or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus,* or *Ancylostoma duodenale*); a parasite (e.g., any protozoa or helminths described herein); a fungus, such as Aspergilli, Candidae, *Coccidioides immitis,* and Cryptococci; a pathogen; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a genetic modification (e.g., antibiotic resistance marker gene); a protein (e.g., a glycoprotein, a metalloprotein, an enzyme, a prion, or an immunoglobulin); a metabolite; a sugar; a lipid; a lipopolysaccharide; a salt; or an ion. Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V. vulnificus, V. cholera, V. parahaemolyticus*), Campylobacterjejuni, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum,* Variola (e.g., *V. major*), Filoviridae (e.g., Ebola virus and Marburg virus), Arenaviridae (e.g., Lassa virus and Machupo virus), *Clostridium perfringens,* any food-borne pathogen (e.g., *Salmonella* species, *Escherichia coli* O157: H7, or *Shigella*), *Chlamydia psittaci, Coxiella burnetii, Staphylococcal aureus, Rickettsia* (e.g., *R. prowazekii* or *R. rickettsii*), Alphavirus (e.g., Venezuelan equine encephalitis virus, eastern equine encephalitis virus, or western equine encephalitis virus), *Vibrio cholerae, Cryptosporidium parvum,* Henipavirus (e.g., Nipah virus), Bunyaviridae (e.g., Hantavirus or Rift Valley fever virus), Flaviviridae (e.g., Japanese encephalitis virus and Yellow fever virus), and *Coccidioides* spp.

In some instances, the sample includes any useful test sample. The test sample can include any useful sample, such as a microorganism, a virus, a bacterium (e.g., enteric bacterium), a fungus, a parasite, a helminth, a protozoon, a cell (e.g., a cell culture), tissue (e.g., tissue homogenates), a fluid, a swab, a biological sample (e.g., blood, such as whole blood, serum, plasma, saliva, urine, cerebral spin fluid, etc.), a buffer, a plant, an environmental sample (e.g., air, soil, and/or water), etc. The test sample can also include a plurality of targets. The sample can be optionally processed (e.g., on-chip or off-chip) in any useful manner (e.g., before or after transporting to the assay area, or even within the assay area), e.g., diluted, mixed, homogenized, lysed, sterilized, incubated, labeled, etc.

Methods

The microfluidic devices and systems herein can be adapted for any useful diagnostic technique. Exemplary diagnostic techniques include particle quantification (e.g., cell counting, differential white blood cell count), sedimentation assays, sandwich assay, nucleic acid assays, agglutination assays, toxin assays, amplification assays, etc.

In one non-limiting instance, the devices and systems herein are adapted to perform a method of conducting a sandwich assay. One exemplary method can include: providing a fluid sample in a channel on a microfluidic device (e.g., a microfluidic disc), the fluid sample including a plurality of particles (e.g., beads) having complexes formed thereon, individual ones of the complexes including a capture agent, a target (e.g., a target analyte), and a label agent, the fluid sample further including a free label agent; providing a density media from a media reservoir to an assay area (e.g., a detection region) of the microfluidic device by applying a first centrifugal force, the media reservoir on the microfluidic disc and in fluid communication with the assay area, the assay area fluidly coupled to the channel, where the density media has a density within a range, an upper bound of the range being lower than a density of the plurality of particles and a lower bound of the range being higher than a density of the fluid sample; transporting the plurality of particles including the complexes through the density media, where the free label agent is restricted from transport through the density media, and where a first plurality of particles having a first property is transported to a first distinct detection location in the assay area and a second plurality of beads having a second property different than the first property is transported to a second distinct detection location in the assay area; detecting a signal from the label agents of the complexes; and generating an electronic detection signal based, at least in part, on the signal detected from the label agents. The method can optionally include, prior to the transporting step, spinning the microfluidic device to apply a second centrifugal force on the plurality of particles, the first and second centrifugal forces being different.

In another non-limiting instance, the devices and systems herein are adapted to perform a method of conducting an assay (e.g., a sedimentation assay). An exemplary method can include: layering a mixture on a density medium in an assay area, where the mixture includes a sample, a first separation layer fluid, and a plurality of sedimentation particles, where the sedimentation particles have a density greater than the density medium, and where the layering a mixture includes forming, with the first separation layer fluid, an interface between the density medium and the sample, between the sample and the sedimentation particles, or between the density medium and the sedimentation particles; subjecting the mixture to a sedimentation force such that the sedimentation particles, if formed, travel through the first separation layer fluid and the density medium to a detection area; and detecting a presence of an analyte of interest in the detection area. Other exemplary assays (e.g., sandwich assays and sedimentation assays) are described in U.S. Pat. Nos. 8,945,914 and 8,962,346, each of which is incorporated herein by reference in its entirety.

In yet another non-limiting instance, the devices and systems herein are adapted to perform a method of conducting an agglutination assay. An exemplary method can include: layering a mixture on a density medium, where the mixture includes a sample and a first population of coated particles (e.g., coated beads) having a first density, where the first population includes a capture agent (e.g., an affinity reagent) for a target (e.g., an analyte of interest), where the first population is configured to form aggregates with the target when present, where the density medium has a minimum density greater than the first density; subjecting the mixture to a sedimentation force such that the aggregates, if formed, travel through the density medium; and detecting a presence of the aggregates in an assay area (e.g., a detection area or a detection region). Other exemplary agglutination assays are described in U.S. Pat. No. 9,244,065, which is incorporated herein by reference in its entirety.

In another non-limiting instance, the devices and systems herein are adapted to perform a method of conducting a toxin activity assay. An exemplary method can include:

generating a plurality of complexes on a plurality of particles (e.g., beads) by action of an active toxin in a fluid sample, individual complexes of the plurality of complexes including a capture agent and a label agent; transporting the plurality of particles including the complexes through a density medium, where the density medium has a density lower than a density of the particles and higher than a density of the fluid sample, and where the transporting occurs, at least in part, by sedimentation; and detecting a signal from the label agents of the plurality of complexes bound to the plurality of particles. Other exemplary toxin activity assays are described in U.S. Pat. No. 9,304,128, which is incorporated herein by reference in its entirety.

In yet another non-limiting instance, the devices and systems herein are adapted to perform a method of conducting a metabolite test. An exemplary system can include: a chamber that includes a fluid, and is configured to accept a sample fluid, where the sample fluid includes a delta-9-THC compound and a metabolite (e.g., a cocaine-based compound, a methamphetamine-based compound, a methamphetamine compound, an amphetamine compound, an opiate-based compound, an MDMA-based compound, a ketamine-based compound, a PCP-based compound, a lysergic acid diethylamide-based compound, or a psilocybin-based compound); and a detection module that, responsive to a centrifugal force being applied to the fluid and the sample fluid, outputs an indication of a level of the delta-9-THC compound and/or the metabolite in the sample fluid.

An exemplary method can include: exposing an agent (e.g., a capture agent, a label agent, or a combination thereof, such as a fluorophore-labelled analyte specific antibody) to a first fluid including at least one of: a free analyte, where the free analyte, if present in the first fluid, originates from a test sample added to the first fluid; or a bound analyte, where the bound analyte, if present in the first fluid, is attached to a first particle having a first density, the agent has a stronger binding affinity for the free analyte than for the bound analyte, the first fluid is in a chamber, the chamber has an open end and a closed end and further includes a second liquid, the second liquid is located at the closed end of the chamber and the first liquid is located between the second liquid and the open end of the chamber; applying a centrifugal force to the chamber, wherein the first particle transfers from the first liquid to the second liquid; irradiating the second liquid to generate a detectable signal in the second liquid (e.g., with light energy to generate fluorescence in the second liquid); and quantifying an amount of free analyte in the second liquid based upon a magnitude of the detectable signal at the second liquid, where the quantification is based upon a threshold value. In some embodiments, the second liquid includes a colloidal suspension of silicon nanoparticles, dextran, poly(ethylene glycol), glycerol, sorbitol, iodixanol, cesium chloride, or perfluorodecalin.

Materials

The present devices and systems can be formed from any useful material. Exemplary materials include a polymer, such as polymethyl methacrylate (PMMA), polyethylene terephthalate (PET, e.g., biaxially-oriented PET or bo-PET), an acrylic polymer, poly(dimethylsiloxane) (PDMS), polycarbonate (PC), cyclo-olefin copolymer (COC), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof, silicon; glass; quartz; fused silica; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organotin compounds), antioxidants (e.g., phenols or amines), and/or UV stabilizers (e.g., benzophenones or salicylates). Such materials can be provided in any useful form, such as in one or more layers that can be laminated to provide the assembled cartridge; and fabricated in any useful manner, such as by way of embossing, etching, injection molding, surface treatments, photolithography, bonding and other techniques.

EXAMPLES

Example 1: Non-Contact Temperature Control System

In an effort to expand the versatility of a rotating microfluidic system by enabling nucleic acid tests with techniques such as loop-mediated isothermal amplification (LAMP), a non-contact heating system was integrated into the platform. An infrared emitter was used to heat aqueous samples and maintain a stable, uniform temperature, e.g. 65° C. to conduct the LAMP reaction. This approach avoids the complexity and cost of incorporating both auxiliary on-disc hardware and a slip-ring for electrically interfacing with the rotating disc (see, e.g., Martinez-Duarte R et al., "The integration of 3D carbon-electrode dielectrophoresis on a CD-like centrifugal microfluidic platform," *Lab Chip* 2010; 10:1030-43; and Abi-Samra K et al., "Electrochemical velocimetry on centrifugal microfluidic platforms," *Lab Chip* 2013; 13:3253-60).

Established heating methods for centrifugal platforms include induction heating (see, e.g., Chen X et al., "Wirelessly adaptable heater array for centrifugal microfluidics and *Escherichia Coli* sterilization," $35^{th}$ *Ann. Int. Conf. IEEE EMBS*, 3-7 Jul. 2013 in Osaka, Japan, pp. 5505-8), which offers a non-contact solution but requires complex circuitry and on-disc electrodes. Infrared laser heating has been used successfully but suffers from inefficiency and added disc complexity by requiring an embedded metal plate to achieve indirect heating of the sample (see, e.g., Kim T H et al., "Fully integrated lab-on-a-disc for nucleic acid analysis of food-borne pathogens," *Anal. Chem.* 2014; 86:3841-8). Thermoelectric heating, commonly used for PCR thermocyclers, has been implemented but requires additional moving parts, such as a linear actuator (see, e.g., Amasia M et al., "Centrifugal microfluidic platform for rapid PCR amplification using integrated thermoelectric heating and ice-valving," *Sens. Actuat. B* 2012; 161:1191-7) or a vacuum pressure system (see, e.g., Roy E et al., "From cellular lysis to microarray detection, an integrated thermoplastic elastomer (TPE) point of care lab on a disc," *Lab Chip* 2015; 15:406-16), to bring the disc into contact with the heating element. In addition, this must be performed on a stationary disc, making real-time detection more difficult.

Herein, we provide a method for uniformly heating an array of biological samples on a centrifugal microfluidic device using an infrared emitter, accurately achieving temperatures required for diagnostic techniques such as isothermal amplification. In particular, we developed an inexpensive non-contact heating system making use of a carbon filament, medium wave infrared emitter that outputs peak wavelengths in the micron range (e.g., of from about 2.4 to about 2.7 µm) that irradiates a PMMA microfluidic disc during slow (e.g., 100 RPM) rotation.

Figure 4A:
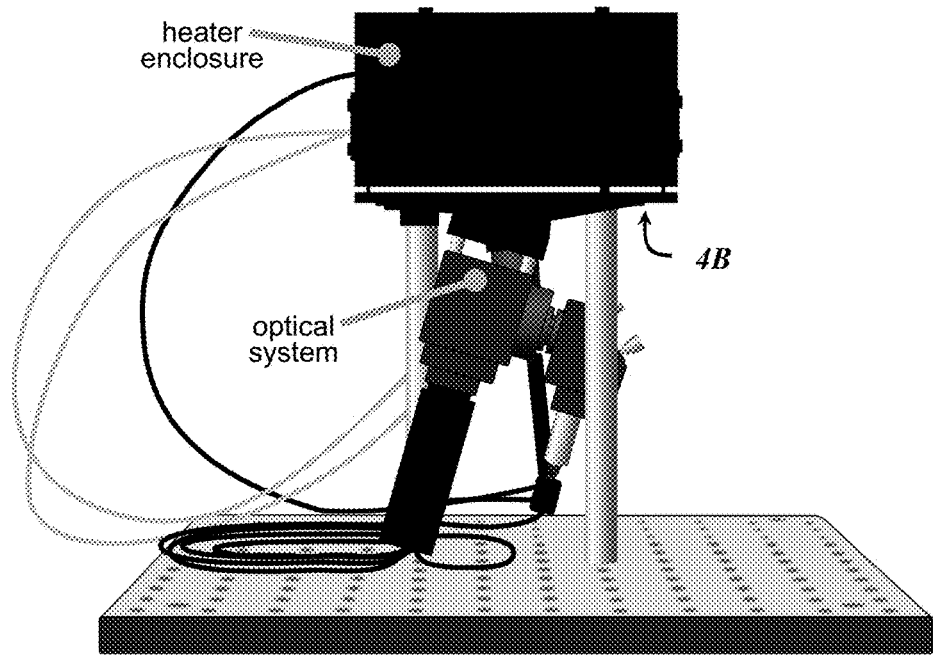
FIG. 4A-4D shows a prototype system including an exemplary non-contact temperature control system mounted over an optical detection module configured for laser-induced fluorescence. Provided are the system (FIG. 4A) including a medium wave infrared emitter and a cooling fan (FIG. 4B). Also provided is an illustration of an exemplary, fully integrated prototype having the heater enclosure hinged over the microfluidic disc, which was mounted to a lower enclosure containing the motor drive, optical system, and control electronics (FIG. 4C), as well as a simplified illustration of the heating system showing the position of the heater over the rotating disc when in operation and the option of a mask for selective heating when combining assays with different temperature requirements (FIG. 4D).
Figure 4B:
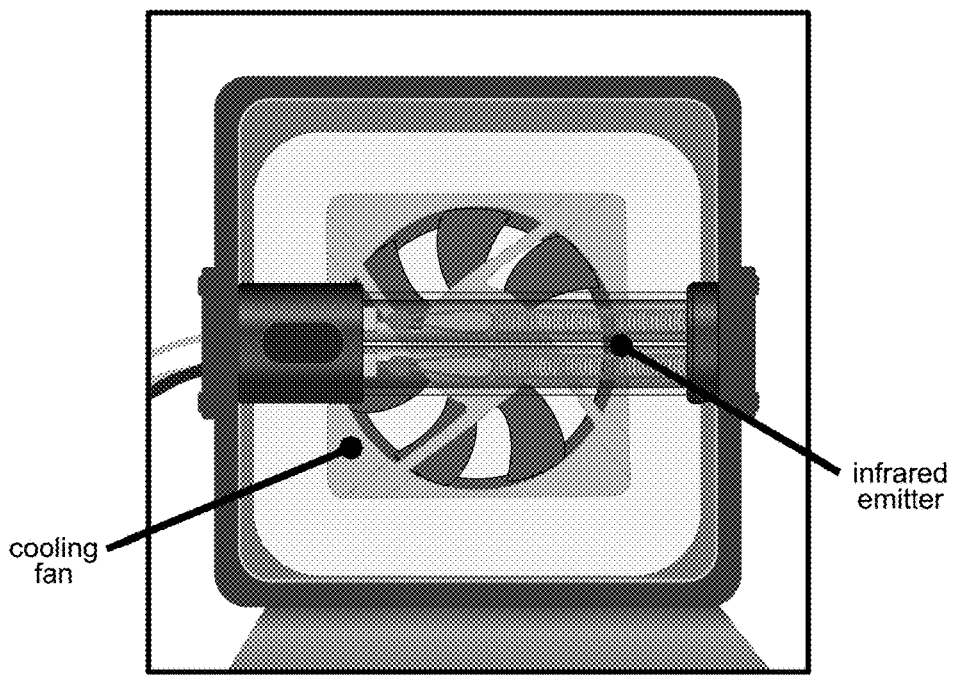

The temperature control system was integrated into an upper enclosure (e.g., the lid) of the instrument in order to heat the disc from above, which avoids exposing sensitive optical and electrical components in the lower enclosure (e.g., the base of the platform) to waste heat. A non-limiting prototype was built around a 3D-printed shell (FIG. 4A) that houses an axial cooling fan and an infrared emitter (FIG. 4B).

The emitter was a custom 100 W medium wave, carbon filament infrared emitter (from Heraeus Noblelight Ltd., Hanau, Germany), which was powered by a 12 VDC source to ensure compatibility with battery power. The emitter had peak wavelengths at about 2.4-2.7 µm and featured a dual-filament design with a gold retro-reflector to focus radiation into a roughly 50 mm by 20 mm region. This focal spot was aligned along a radial section of the microfluidic disc, centered with the assay area (e.g., a reaction chamber). The medium wave radiation band emitted by the heater closely matched the peak absorption wavelengths of water, enabling efficient heating of the low-volume (e.g., 10 µL) aqueous samples contained in the disc.

In some instances, prior to heating the disc, an adhesive backed foil layer was applied over the center of the disc (e.g., over the sample ports) to prevent heating of the sealing barrier, which can cause leakage. With the disc mounted on the motor hub and the lid/heater enclosure closed, the infrared emitter was powered while the disc was spun at low speed (e.g., less than about 300 RPM) to achieve temperature uniformity. In one non-limiting instance, the disc was rotated at 100 RPM, and the heater was powered at 28 W to achieve uniform heating to 65° C. The cooling fan was operated at low speed during heating to minimize heat build-up within the heater enclosure and operated at high speed when the reaction was complete to provide forced convective cooling of the samples.

Figure 4C:
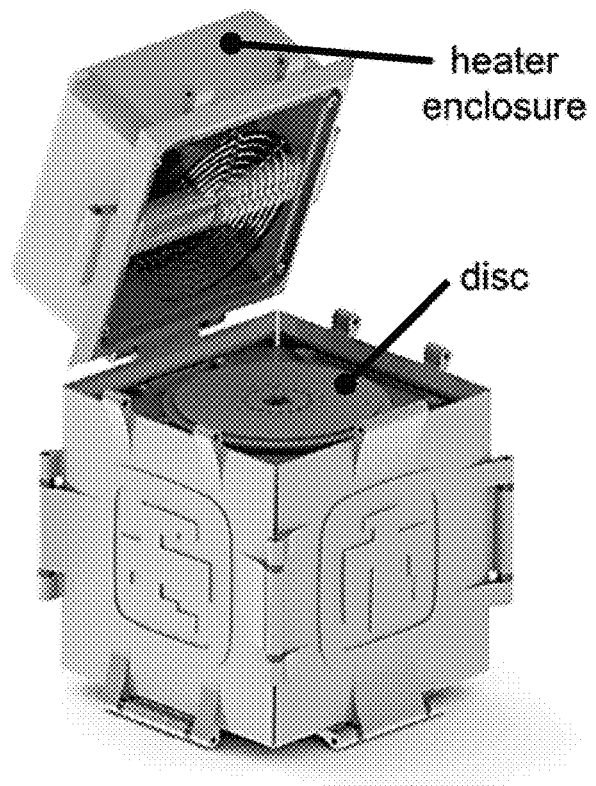
Figure 4D:
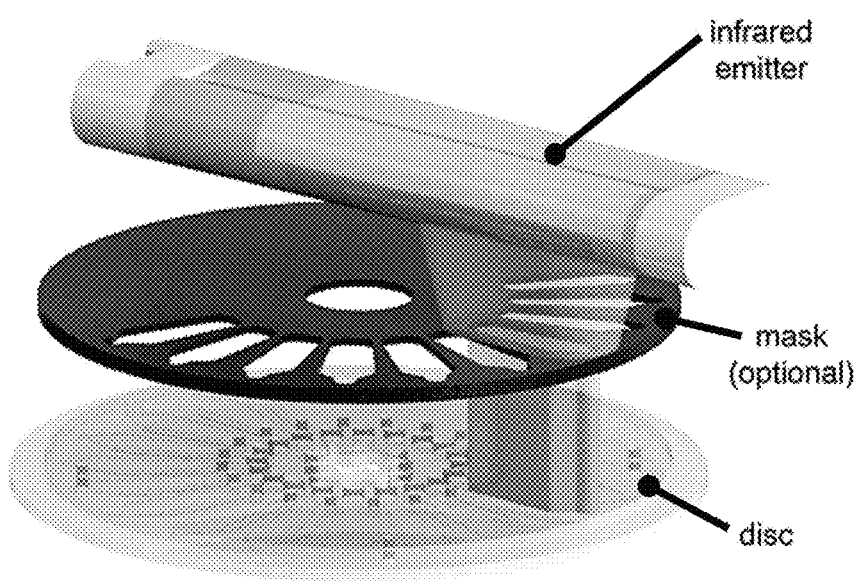
Figure 5A:
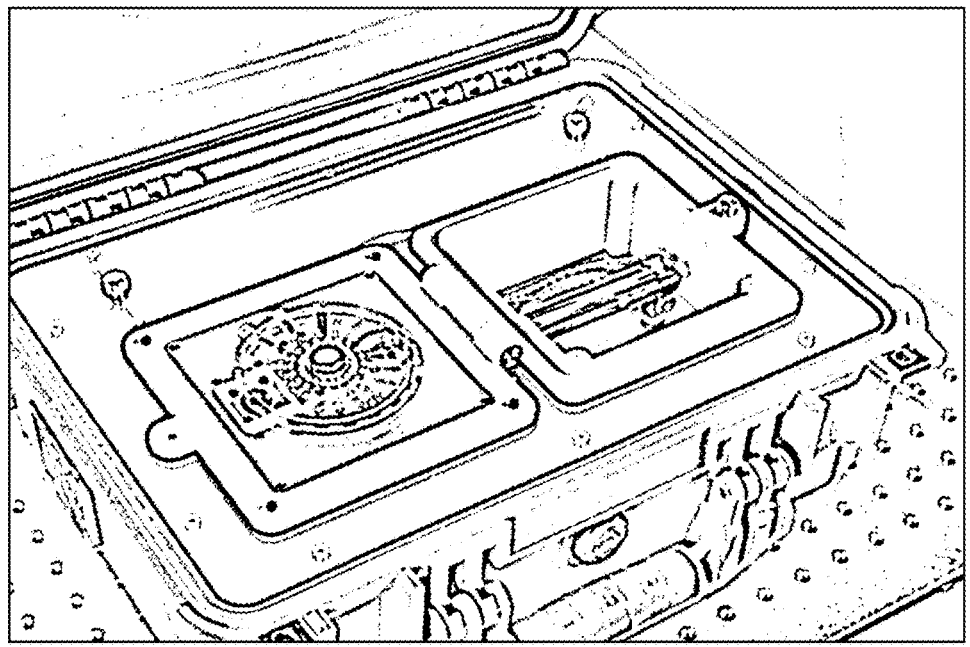
FIG. 5A-5B shows an exemplary system in shown in both the open position (FIG. 5A) and the closed position (FIG. 5B). The heater enclosure can optionally feature a window for observation via infrared camera, and the carbon filament infrared emitter can be seen positioned over the disc when in the closed position.
Figure 5B:
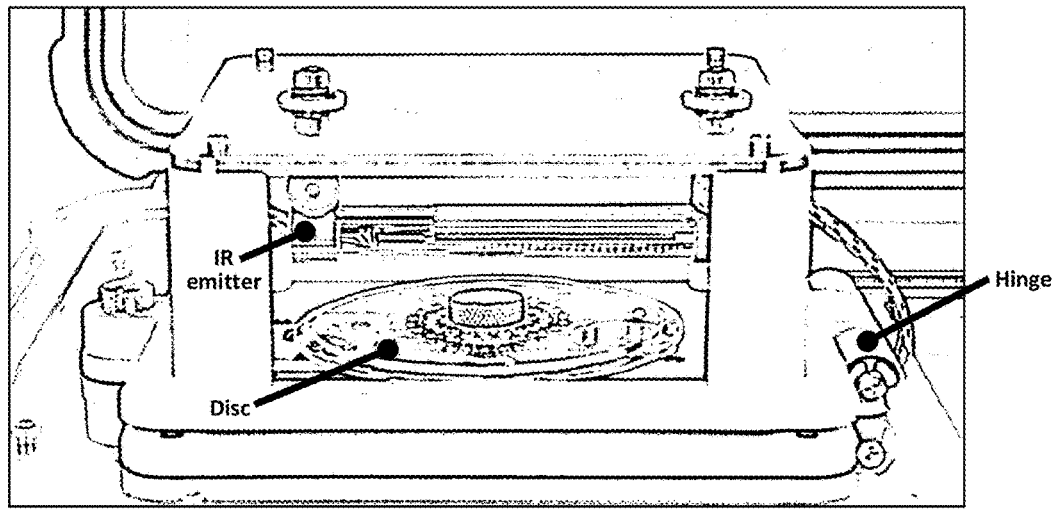

The modules can be integrated into a single system. An exemplary non-contact heating system with a fully enclosed instrument is shown in FIG. 4C, and a simplified rendering of the heating concepts is shown in FIG. 4D. In another embodiment, the non-contact heating system is mounted in a hinged enclosure (FIG. 5A) in order to swivel the heater into position over the disc when ready for operation (FIG. 5B). These modules, along with a power supply and control electronics, can be housed in a Pelican case.

Additional upgrades made to the SpinDx instrumentation included a single brushless servomotor drive system to replace a multi-motor system, which relies on the coordination of a low power brushed DC motor, hobby-grade servo motor, and stepper motor. A single brushless servomotor with a 12-bit absolute encoder (2232S012BX4AES-4096, Dr. Fritz Faulhaber GmbH & Co. KG, Schoenaich, Germany) can provide both the high-speed spin operation for centrifugation through the density medium and precise indexing for the end-point detection step. Optionally, optical switches can be configured to interact with markings on the disc for home positioning.

In addition, a new detection module (e.g., an optical system) can be implemented for compatibility with any useful dye, such as the Syto® 9 fluorescent dye (Thermo Fisher Scientific Inc., Waltham, Mass.), which does not require the sample to be at room temperature for detection, enabling real-time fluorescence monitoring during nucleic acid amplification. The detection module can include a laser diode module, one or more photomultiplier tubes, and excitation and emission filters. This could allow for the termination of a reaction as soon as a detection threshold has been reached, potentially reducing analysis time and power consumption. Other useful modifications can be implemented to enhance and/or simplify device rotation and/or detection.

Efficient, non-contact heating makes available a more complete panel of sensitive diagnostics that require temperature-dependent chemistries without substantially increasing device complexity. This keeps instrument cost low and maintains the viability of a disposable disc. In addition, the benefits of temperature control capabilities extend beyond enabling nucleic acid tests and include enhancement of immunoassay kinetics through heating as well as the ability for the instrument to operate in extreme climates. The platform, which is composed of a compact optical system for laser-induced fluorescence (LIF) detection, a quiet brushless motor, and an efficient non-contact heater, offers an easy-to-use system capable of performing sensitive pathogen screening in a lab-free environment.

Example 2: Temperature Calibration of the Non-Contact Heating System

Calibration of the heating system was performed by first fabricating a disc with a T-type micro-thermocouple (IT-24P, Physitemp Instruments Inc., Clifton, N.J.), which had a 125 µm diameter, embedded in one of the assay areas. This thermocouple was connected to a custom hub with a built-in slip ring, allowing the thermocouple to rotate with the disc while heating while the output wiring remained stationary for voltage measurement. The slip ring output was connected to a linearizing circuit (Omega® TAC80B-T, Omega Engineering, Inc., Stamford, Conn.) that provided a 1 mV/° C. signal, which was collected using data acquisition hardware and LabVIEW. In parallel with the thermocouple measurement, an infrared camera (FLIR T420, FLIR Systems, Inc., Boston, Mass.) was positioned above the disc to measure the top surface temperature of the disc.

Figure 6A:
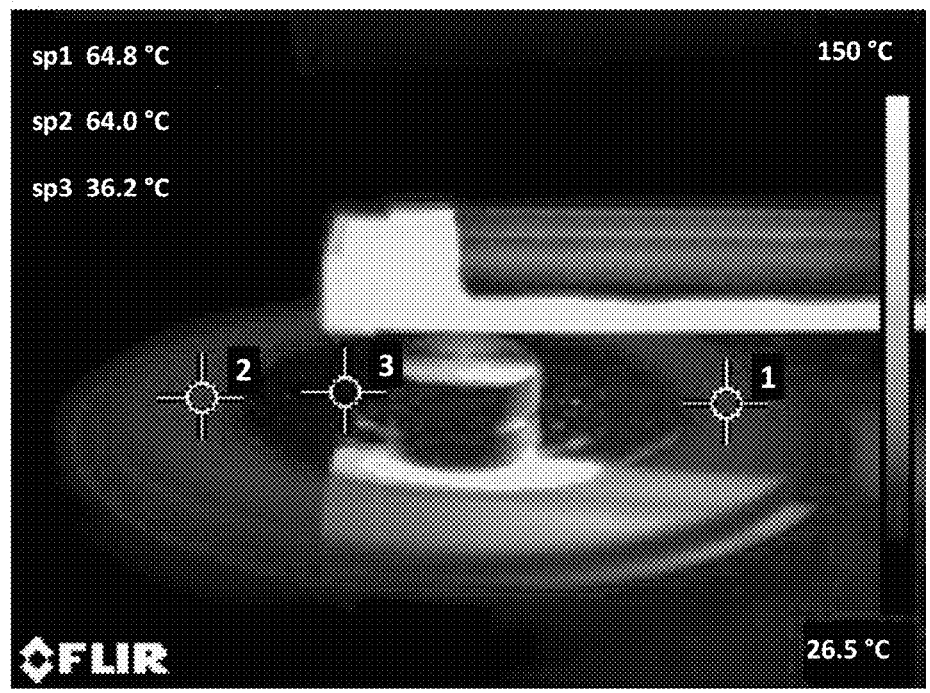
FIG. 6A-6B shows temperature calibration of an exemplary heating system. Provided are a thermal image captured by an infrared camera to monitor disc temperature (FIG. 6A) and a calibration curve generated by correlating surface temperature measurements with sample temperature measurements collected using an embedded micro-thermocouple (FIG. 6B).
Figure 6B:
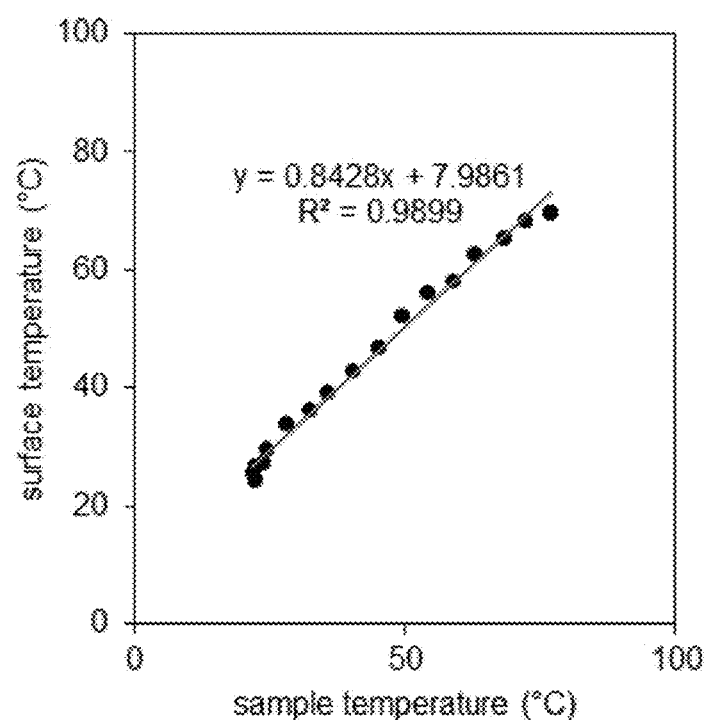

As shown in FIG. 6A, temperature data were collected from the top surface of the disc, namely at location 2 in FIG. 6A, which was directly over the assay areas. Collected data were correlated with true sample temperatures measured using the embedded thermocouple. This correlation, plotted in FIG. 6B, was then used for open loop operation of the disc, requiring only a simple infrared camera measurement to confirm setpoints.

Example 3: On-Chip Amplification and Detection of *E. coli*

Figure 7:
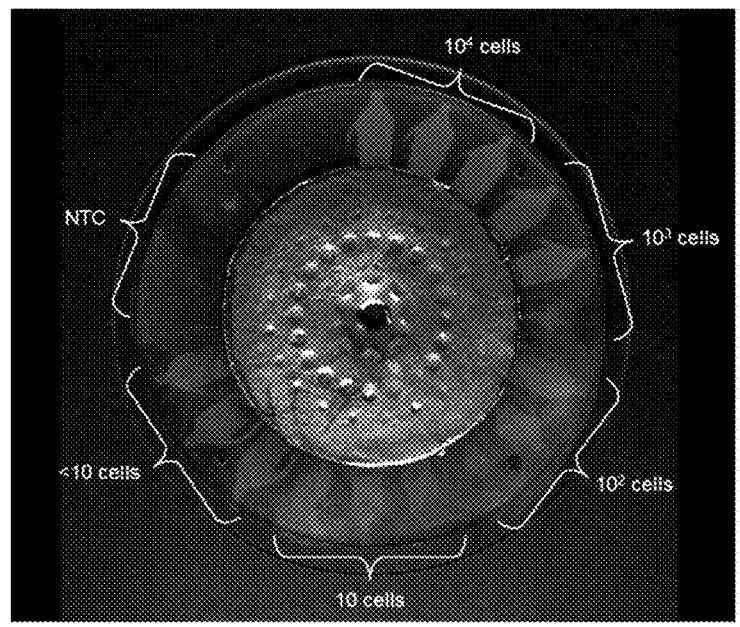
FIG. 7 shows a fluorescence image of a microfluidic disc after successful isothermal amplifications of an *E. coli* target for a serial dilution from <10 cells/µL to $10^4$ cells/µL performed in triplicate, as compared to a negative control (labeled "NTC").

The calibrated heating system was tested by amplifying a heat-killed *E. coli* O157:H7 target (Cat. No. 50-95-90, KPL, Inc., Gaithersburg, Md.) using a loop-mediated isothermal amplification (LAMP) reaction with QUASR chemistry (see, e.g., Ball C S et al., "Quenching of unincorporated amplification signal reporters in reverse-transcription loop-mediated isothermal amplification enabling bright, single-step, closed-tube, and multiplexed detection of RNA viruses," *Anal. Chem.* 2016; 88:3562-8). In brief, Cy5-labeled primers were employed to target the stx1 gene. With a 10× serial dilution of the target DNA from $10^4$ cells/µL to ~1 cell/µL, sets of 10 µL reaction were run in triplicate for each template concentration along with a negative template control (NTC). The disc was heated to 65° C., incubated for 45 minutes, and then cooled on ice. Fluorescence was then measured using a gel imager (ProteinSimple, Bio-Techne Corp., Minneapolis, Minn.). Successful Detection Over the Range of Dilutions was Observed (FIG. 7).

Example 4: Exemplary Portable, Non-Contact Heating System

Figure 8A:
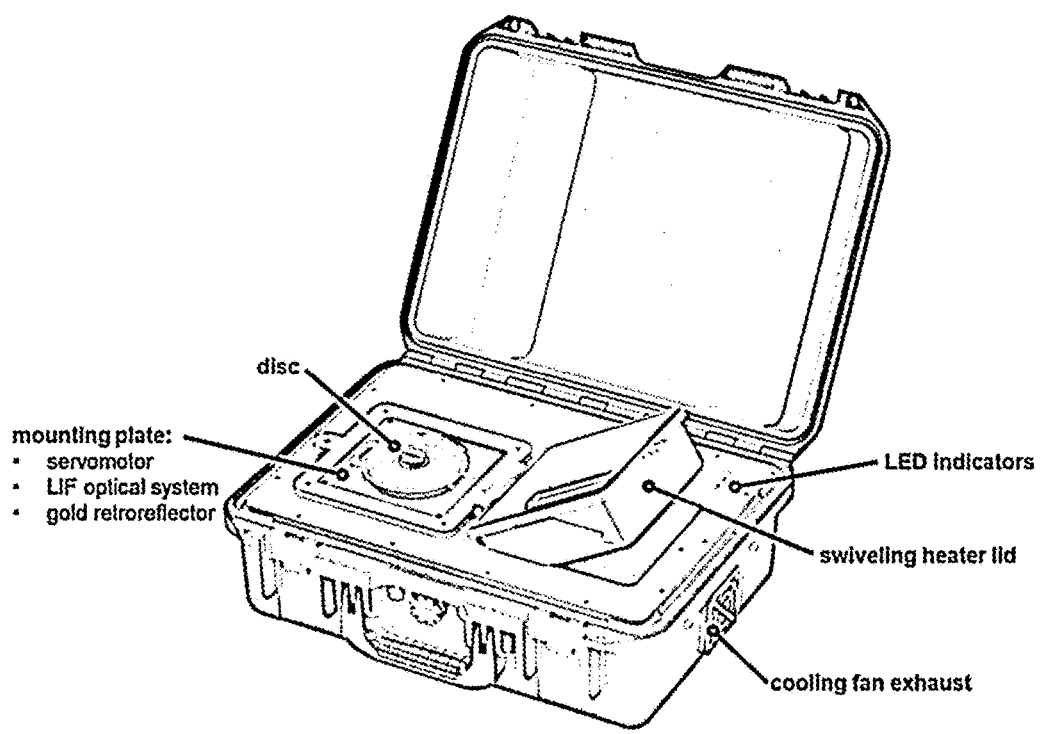
FIG. 8A-8B shows another exemplary portable prototype having a mounting plate configured to support a microfluidic disc and to engage with components of the motor module and the optical detection module. Provided are illustrations of the exemplary, fully integrated prototype in a perspective view (FIG. 8A) and exemplary internal components of the prototype (FIG. 8B).
Figure 8B:
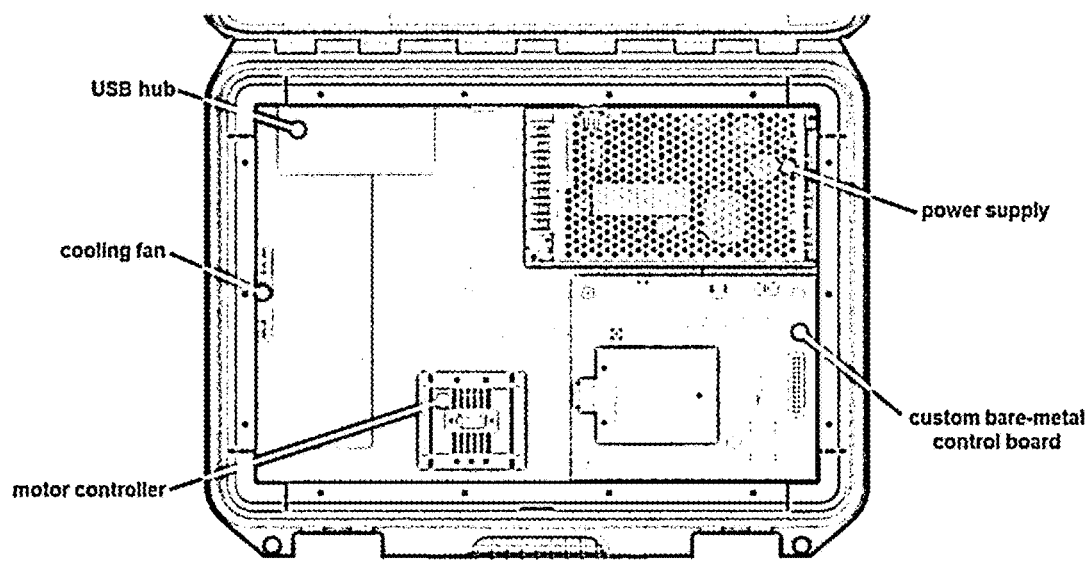

FIG. 8A-8B provides further designs for an exemplary portable, non-contact heating system. The system can include various components incorporated into a single enclosed case.

Figure 9A:
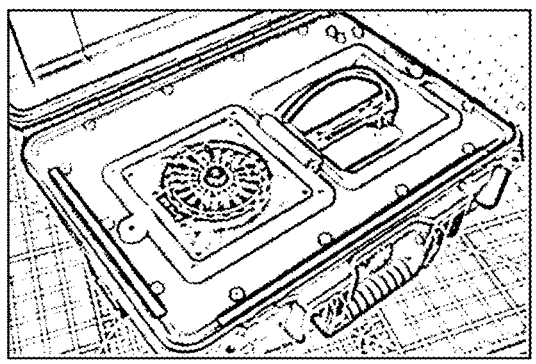
FIG. 9A-9B shows an exemplary system in shown in both the open position (FIG. 9A) and the closed position (FIG. 9B). The position of the heater (e.g., a carbon filament infrared emitter) from the microfluidic disc can be adjusted in any useful manner to provide desired heating extent and location in the closed position.
Figure 9B:
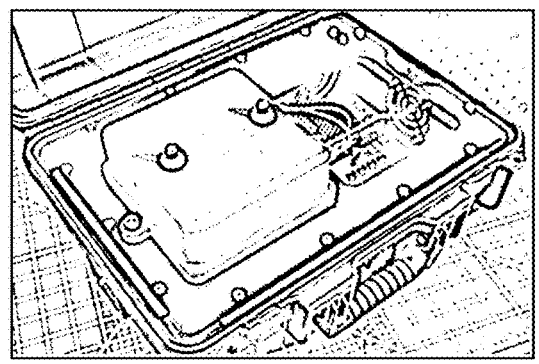
Figure 10A:
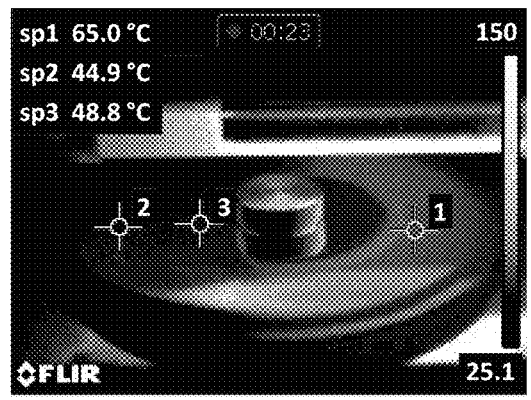
FIG. 10A-10D shows temperature calibration of an exemplary heating system. Provided are time-lapsed thermal images captured by an infrared camera to monitor disc temperature during heating (FIG. 10A), after heating but with an attached reflective mask (FIG. 10B), and after removal of the reflective mask (FIG. 10C-10D).
Figure 10B:
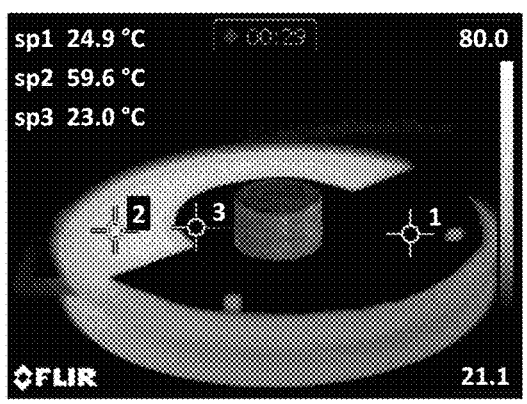
Figure 10C:
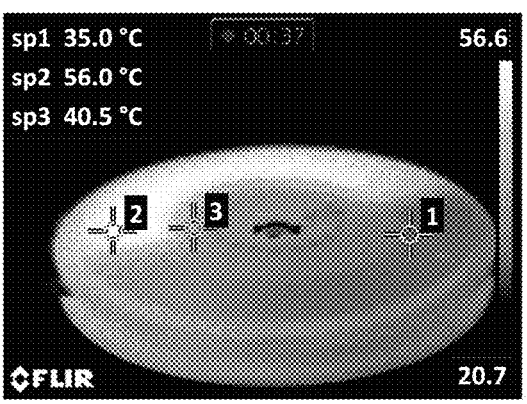
Figure 10D:
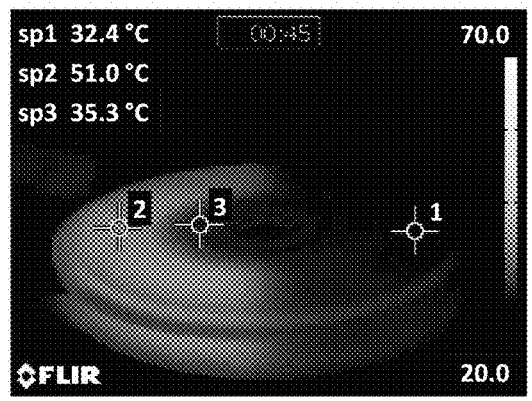

One component can include the non-contact temperature control module, which can be provided as an upper enclosure having the non-contact heater and a lower enclosure having a mounting plate configured to support the microfluidic disc (FIG. 8A). The lower enclosure can further include additional components or modules to rotate the disc and to detect one or more targets (e.g., a servo motor, a reflector, an optical switch, circuitry, and/or a LIF optical system). Provided are photographs of the enclosure in the open position (FIG. 9A, in which the upper and lower enclosures are separated) or in the closed position (FIG. 9B, in which the upper and lower enclosures are in contact).

The system can further include other components and modules. As seen in FIG. 8B, the system can include various components within a lower compartment of the case. This lower compartment underlies the enclosure, which has the non-contact heating temperature control module, the microfluidic device, the motor module, and the detection module. The lower component can include useful components such as an input/output hub (e.g., a USB hub), a cooling fan, a power supply, a control board, and a motor controller.

In some embodiments, a reflective mask was employed to provide different temperature zones. The location of such zones can be controlled by placing a reflective mask in contact with regions of the disc requiring a lower temperature. For instance, a reflective mask can be used to shield immunoassay chambers during heating, achieving two temperature zones: one hotter zone for nucleic acid amplification tests and another cooler zone for immunoassays or any other assay not requiring elevated temperatures.

As seen in FIG. 10A-10D, an elevated temperature zone (e.g., from about 55° C. to 65° C.) can be maintained for microfluidic chambers configured to perform LAMP reactions (e.g., including one or more reagents to conduct LAMP), and a lower temperature zone (e.g., from about 20° C. to 50° C.) for microfluidic chambers configured to perform immunoassays (e.g., including one or more reagents to conduct an immunoassay).

Example 5: Detection of Enteric Bacteria Using On-Chip LAMP Amplification

Figure 11A:
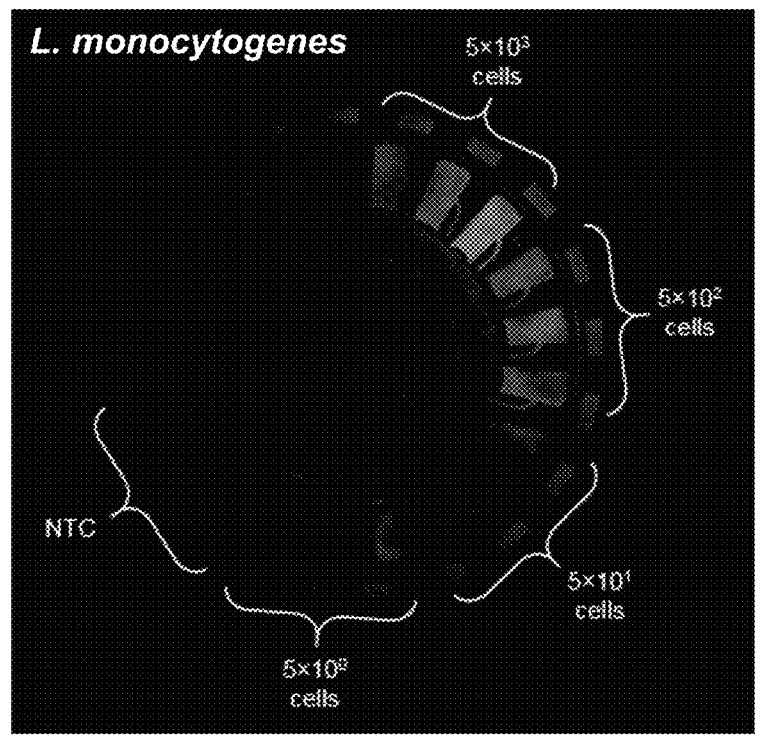
FIG. 11A-11C shows fluorescence images of a microfluidic disc after amplifications of various targets, including *L. monocytogenes* (FIG. 11A), *C. jejuni* (FIG. 11B), and *E. coli* (FIG. 11C) for the provided serial dilutions, as compared to a negative control (labeled "NTC").
Figure 11B:
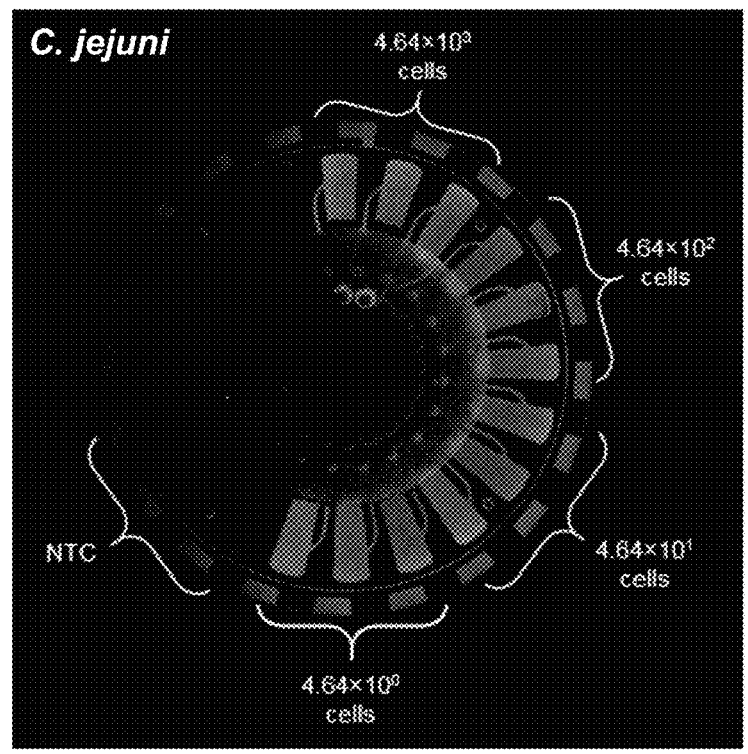
Figure 11C:
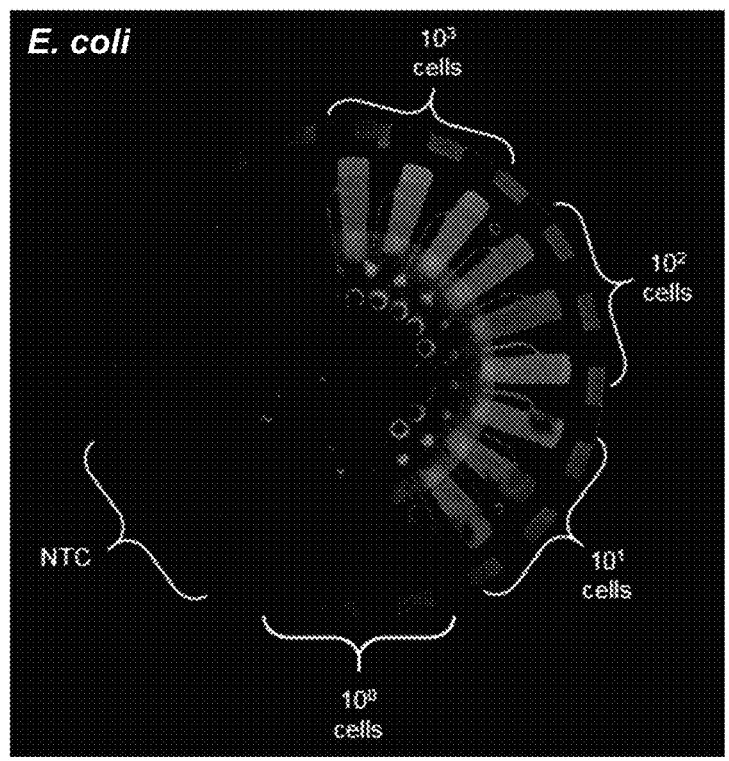
Figure 12A:
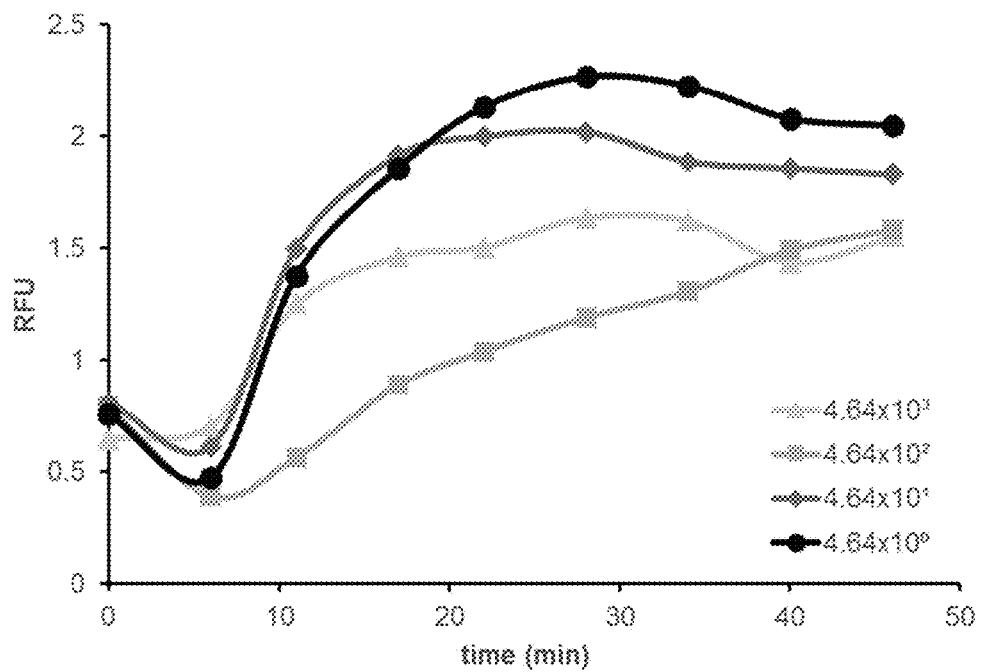
FIG. 12A-12C provides detection of *C. jejuni* amplification via LAMP using a SYTO® 9 dye. Provided are a graph quantifying real-time fluorescence detection for various serial dilutions of *C. jejuni* (FIG. 12A), a fluorescence image of microfluidic device after amplification of the target and using a SYTO® 9 dye (FIG. 12B), and another fluorescence image of the same microfluidic device showing confirmation using a secondary Cy5 dye (FIG. 12C).
Figure 12B:
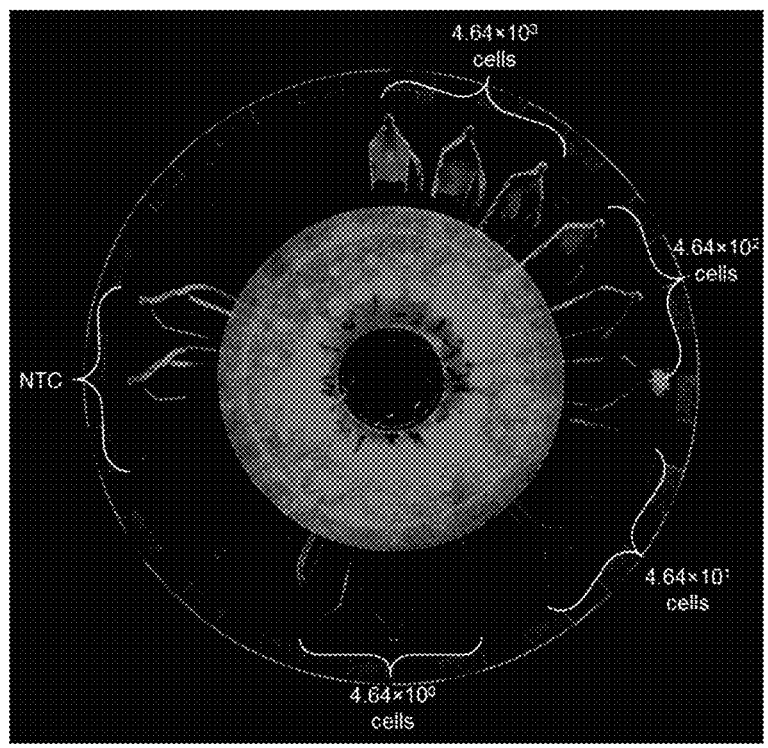
Figure 12C:
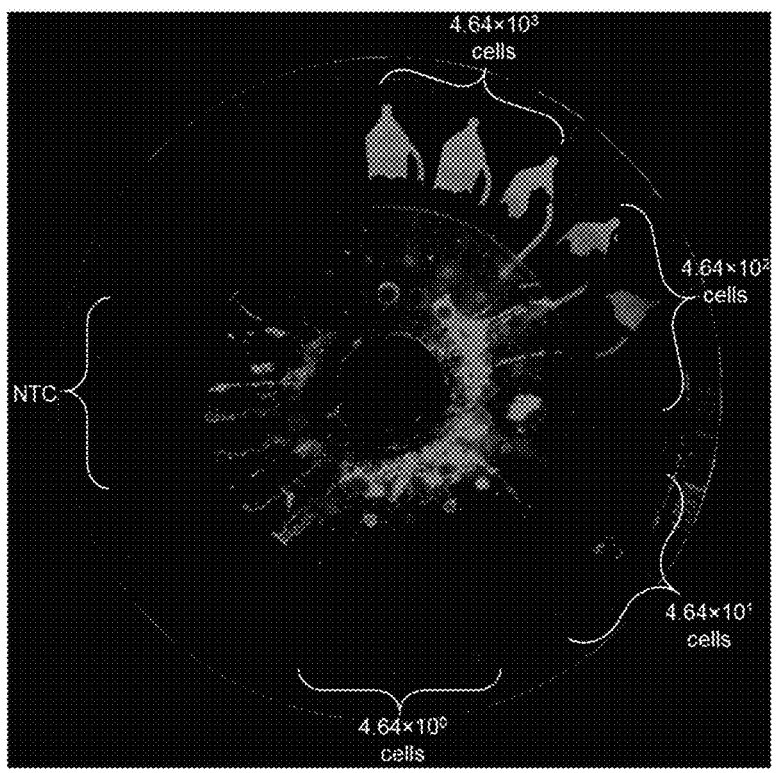

By employing a portable non-contact heating system, a panel of enteric bacteria was detected on-chip by employing LAMP. Successful detection over the range of dilutions was observed (FIG. 11A-11C). Further studies included real-time fluorescence detection of C. jejuni amplification via LAMP using a SYTO® 9 dye (FIG. 12A-12C).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A non-contact temperature control system for a microfluidic device, the temperature control system comprising:
    an infrared emitter configured to emit at a wavelength of from about 1 µm to about 5 µm and positioned to direct radiation to a first surface of the microfluidic device;
    a reflector configured to reflect radiation that is collected from a second surface of the microfluidic device, wherein the second surface opposes the first surface; and
    a focal point of the emitter configured to be positioned on or within an assay area, or a portion thereof, of the microfluidic device,
    wherein the focal point of the emitter and a vertex of the reflector are aligned along a central axis.

2. The temperature control system of claim 1, further comprising:
    a mask configured to be disposed between the emitter and the microfluidic device, wherein the mask comprises an opening to provide selective heating of a first portion of the microfluidic device and a shielded region to provide selective masking of a second portion of the microfluidic device.

3. The temperature control system of claim 1, further comprising:
    a detection module configured to detect a signal from the assay area.

4. The temperature control system of claim 3, further comprising:
    a cooling fan configured to be in proximity to the emitter.

5. The temperature control system of claim 4, wherein the emitter and the cooling fan are configured to be positioned above the microfluidic device, and wherein the reflector and the detection module are configured to be positioned below the microfluidic device.

6. The temperature control system of claim 1, wherein the focal point is configured to be positioned on or within the assay area containing a density media.

7. The temperature control system of claim 6, wherein the assay area includes a narrowed region and the focal point is configured to be positioned on or within the narrowed region.

8. The temperature control system of claim 1, wherein the emitter has a peak wavelength of from about 2 µm to about 3 µm.

9. A system for providing non-contact heating, the system comprising:
    a microfluidic disc comprising:
        a substrate; and
        an assay area disposed, at least in part, within or on the substrate;
    a non-contact temperature control module comprising:
        an infrared emitter configured to emit at a wavelength of from about 1 µm to about 5 µm and positioned to direct radiation to a first surface of the microfluidic device; and a focal point of the emitter configured to be positioned on or within an assay area, or a portion thereof, of the microfluidic device;

a motor module configured to be coupled to the microfluidic disc and to spin the microfluidic disc in response to a motor control signal; and a detection module configured to detect a signal from one or more label agents present in the assay area, wherein the detection module is configured to generate an electronic detection signal based, at least in part, on the signal from the one or more label agents.

10. The system of claim 9, further comprising:
a reflector configured to reflect radiation that is collected from a second surface of the microfluidic device, wherein the second surface opposes the first surface, and wherein the focal point of the emitter and a vertex of the reflector are aligned along a central axis.

11. The system of claim 9, further comprising:
a processing device coupled to the motor module and the detection module, wherein the processing device is configured to generate the motor control signal and provide the motor control signal to the motor module, and wherein the processing device is further configured to receive the electronic detection signal from the detection module.

12. The system of claim 9, further comprising:
a mask configured to be disposed between the emitter and the microfluidic device, wherein the mask comprises an opening to provide selective heating of a first portion of the microfluidic device and a shielded region to provide selective masking of a second portion of the microfluidic device.

13. The system of claim 9, further comprising:
a cooling fan configured to be in proximity to the emitter.

14. The system of claim 9, wherein the assay area further comprises a first density media.

15. The system of claim 13, wherein the assay area further comprises a first plurality of particles in a fluid sample, and wherein the first density media has a density lower than a density of the first plurality of particles and higher than a density of the fluid sample.

16. The system of claim 14, wherein the assay area further comprises a second density media, a second plurality of particles, a plurality of complexes, a plurality of cells, a plurality of sedimentation particles, and/or a first separation layer fluid.

17. The system of claim 10, further comprising:
an upper enclosure configured to contain the emitter; and
a lower enclosure configured to contain the reflector, the motor module, and the detection module.

18. The system of claim 15, wherein the upper enclosure is further configured to contain a cooling fan and maintain the cooling fan in proximity to the emitter.

19. The system of claim 15, wherein the lower enclosure is further configured to contain the microfluidic disc.

20. A system for providing non-contact heating, the system comprising:
a microfluidic disc comprising:
a substrate, wherein the substrate at least in part defines a channel;
a sample port in fluid communication with the channel and configured to receive a plurality of particles in a fluid sample; and
a detection region coupled to the channel and defined at least in part by the substrate and configured to contain a density media, wherein the density media has a density lower than the plurality of particles and higher than a density of the fluid sample;
wherein the channel and detection region are configured to transport the plurality of particles in the fluid sample from the channel through the density media responsive to a centrifugal force, and wherein at least a portion of the fluid sample is restricted from transport through the density media;
a non-contact temperature control module comprising:
an infrared emitter configured to emit at a wavelength of from about 1 μm to about 5 μm and positioned to direct radiation to a first surface of the microfluidic device;
a reflector configured to reflect radiation that is collected from a second surface of the microfluidic device; and
a focal point of the emitter configured to be positioned on or within the detection region, or a portion thereof, of the microfluidic device, wherein the second surface opposes the first surface, and wherein the focal point of the emitter and a vertex of the reflector are aligned along a central axis;
a motor module configured to be coupled to the microfluidic disc, to receive a motor control signal, and to spin the microfluidic disc responsive to the motor control signal;
a detection module positioned to detect a signal from one or more label agents affixed to the plurality of particles, wherein the detection module is configured to generate an electronic detection signal based, at least in part, on the signal from the one or more label agents; and
a processing device coupled to the motor module and the detection module, wherein the processing device is configured to generate the motor control signal and provide the motor control signal to the motor module, and wherein the processing device is further configured to receive the electronic detection signal from the detection module.

* * * * *

UNITED STATES PATENT AND TRADEMARK OFFICE
CERTIFICATE OF CORRECTION

PATENT NO. : 10,406,528 B1
APPLICATION NO. : 15/669426
DATED : September 10, 2019
INVENTOR(S) : Christopher Phaneuf and Chung-Yan Koh It is certified that error appears in the above-identified patent and that said Letters Patent is hereby corrected as shown below:

In the Specification

Column 1, Line 16, under the heading STATEMENT OF GOVERNMENT INTEREST, add the following statement after the word 'Administration':
--and under Grant No. R01AI098853 awarded by the National Institute of Allergy and Infectious Diseases of the National Institutes of Health--.

Signed and Sealed this
Twenty-eighth Day of January, 2020

Andrei Iancu
*Director of the United States Patent and Trademark Office*